(12) United States Patent
Ostermeier

(10) Patent No.: US 8,492,122 B2
(45) Date of Patent: Jul. 23, 2013

(54) MOLECULAR SWITCHES AND METHODS FOR MAKING AND USING THE SAME

(75) Inventor: Marc Ostermeier, Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 0 days.

(21) Appl. No.: 10/507,466

(22) PCT Filed: Mar. 10, 2003

(86) PCT No.: PCT/US03/07380
§ 371 (c)(1),
(2), (4) Date: Sep. 10, 2004

(87) PCT Pub. No.: WO03/078575
PCT Pub. Date: Sep. 25, 2003

(65) Prior Publication Data
US 2005/0181366 A1 Aug. 18, 2005

Related U.S. Application Data

(60) Provisional application No. 60/362,588, filed on Mar. 11, 2002.

(51) Int. Cl.
*C12N 15/64* (2006.01)
*C12N 15/66* (2006.01)
*C07H 21/02* (2006.01)
*C07H 21/04* (2006.01)

(52) U.S. Cl.
USPC ..... 435/91.41; 435/91.4; 536/23.1; 536/23.4; 536/23.7

(58) Field of Classification Search
USPC .............. 536/23.1, 23.4, 24.1, 23.7; 530/300, 530/350; 424/192.1; 435/91.4, 91.41
See application file for complete search history.

(56) References Cited

U.S. PATENT DOCUMENTS

| | | | |
|---|---|---|---|
| 6,469,154 B1 * | 10/2002 | Tsien et al. | 536/23.5 |
| 6,485,912 B1 * | 11/2002 | Heintz et al. | 435/6 |
| 6,596,485 B2 * | 7/2003 | Anderson et al. | 435/6 |
| 6,867,035 B2 * | 3/2005 | Ong | 435/287.2 |
| 7,029,847 B2 * | 4/2006 | Joung et al. | 435/6 |
| 7,135,176 B2 * | 11/2006 | Norris et al. | 424/139.1 |
| 2001/0003650 A1 | 6/2001 | Anderson et al. | |

OTHER PUBLICATIONS

Siegel et al., 2000, Methods in Enzymology, vol. 327, p. 249-259.*
Kratz et al., 1999, PNAS, vol. 96, pp. 1915-1920.*
Lacatena et al., 1994, PNAS, vol. 91, pp. 10521-10525.*
Doi et al., 1999, FEBS Letters, vol. 453, p. 305-307.*
Manoil et al., 1990, Journal of Bacteriology, vol. 172, No. 2, p. 515-518.*
Mountford et al., 1995, TIG, vol. 11, No. 5, p. 179-184.*
McWherter et al., 1999, Biochemistry, vol. 38, p. 4564-4571.*
Skolnick et al., 2000, Trends in Biotech, vol. 18, p. 34-39.*
Tomasinsig et al., 2005, Current Protein and Peptide Science, vol. 6, p. 23-34.*
Smallwood et al., 2002, Virology, vol. 304, p. 135-145.*
Chattopadhyay et al., 2004, Virus Research, vol. 99, p. 139-145.*
Fox et al., 2001, Protein Science, vol. 10, p. 622-630.*
Sheridan, et al., "A new way to rapidly create functional, fluorescent fusion proteins: random insertion of GFP with an in vitro transposition reatction," BMC Neuroscience, Jun. 2002, vol. 3, No. 7, pp. 1-11.
Siegel, et al., "Green Fluorescent Protein-Based Sensors for Detecting Signal Transduction and Monitoring Ion Channel Function," Methods in Enzymology, 2000, vol. 327, p. 249-259, especially pp. 249-252.
U.S. Appl. No. 10/588,114, filed Aug. 1, 2007, Ostermeier, Marc A.

* cited by examiner

*Primary Examiner* — Shin-Lin Chen
(74) *Attorney, Agent, or Firm* — Johns Hopkins Technology Transfer

(57) ABSTRACT

The invention provides molecular switches which couple external signals to functionality and to methods of making and using the same. The switches according to the invention can be used, for example, to regulate gene transcription, target drug delivery to specific cells, transport drugs intracellularly, control drug release, provide conditionally active proteins, perform metabolic engineering, and modulate cell signaling pathways. Libraries comprising the switches and expression vectors and host cells for expressing the switches are also provided.

6 Claims, 10 Drawing Sheets

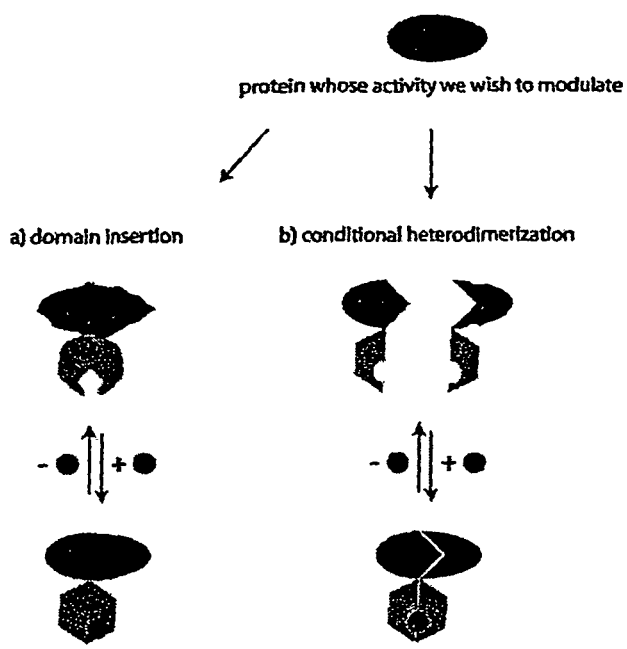
protein whose activity we wish to modulate
a) domain insertion
b) conditional heterodimerization
FIG. 1A
FIG. 1B
Enzyme (Protein A)
Binding Protein (Protein B)
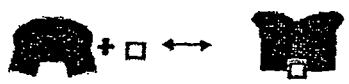
Enzyme-Binding Protein Hybrid.
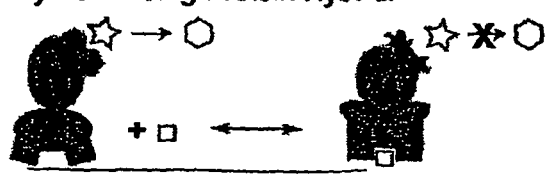
FIG. 1C

FIG. 3A a) Gene Transcription

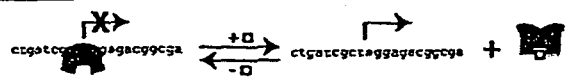

FIG. 3B b) Signal Transduction

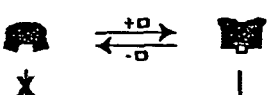

Apoptosis, Differentiation, etc.

FIG. 3C c) Targeted Drug Delivery

healthy cell     diseased cell or pathogen

□   surface protein unique or present at higher level on diseased cell or pathogen ☆   drug

FIG. 3D d) Drug Transport

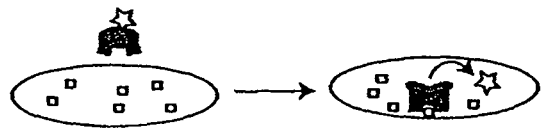

□   small molecule, protein or other signal (e.g. pH change) inside cell

☆   drug

🯄   protein with domain that is taken up by cells (e.g. transferrin)

FIG. 3E e) Conditionally-active toxic proteins

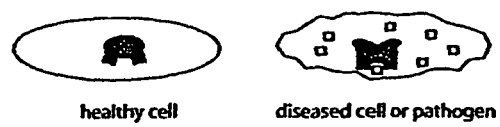

healthy cell     diseased cell or pathogen

🯄   inactive form of toxin

🯅   active form of toxin

□   protein or small molecule unique or present at higher level in diseased cell or pathogen

FIG. 3F f) Metabolic Engineering

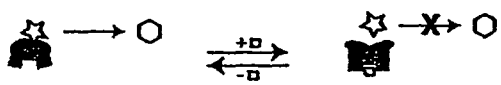

FIG. 3G g) Biosensors

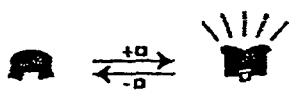

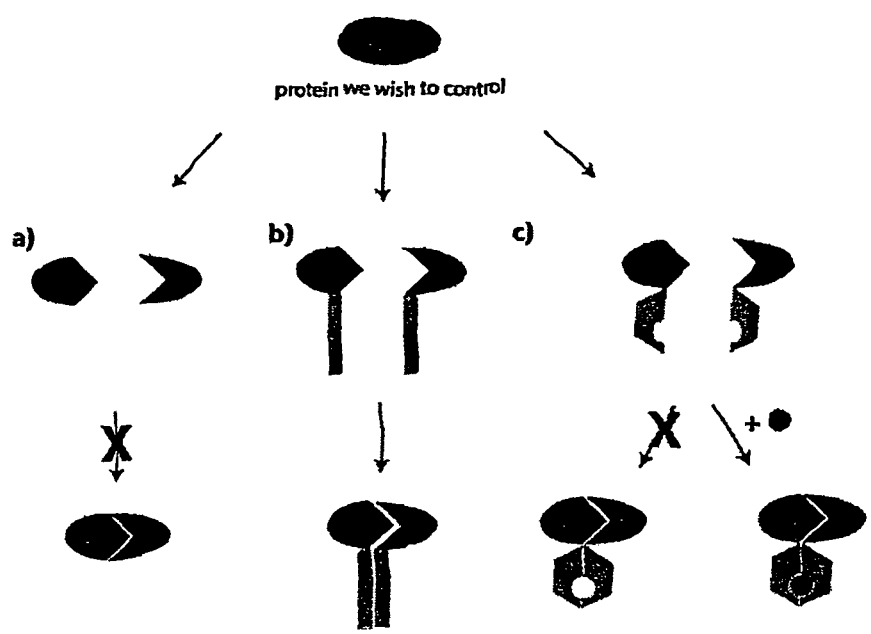

Frequency of active heterodimers of Neo whose assembly is assisted by antiparallel leucine zippers.

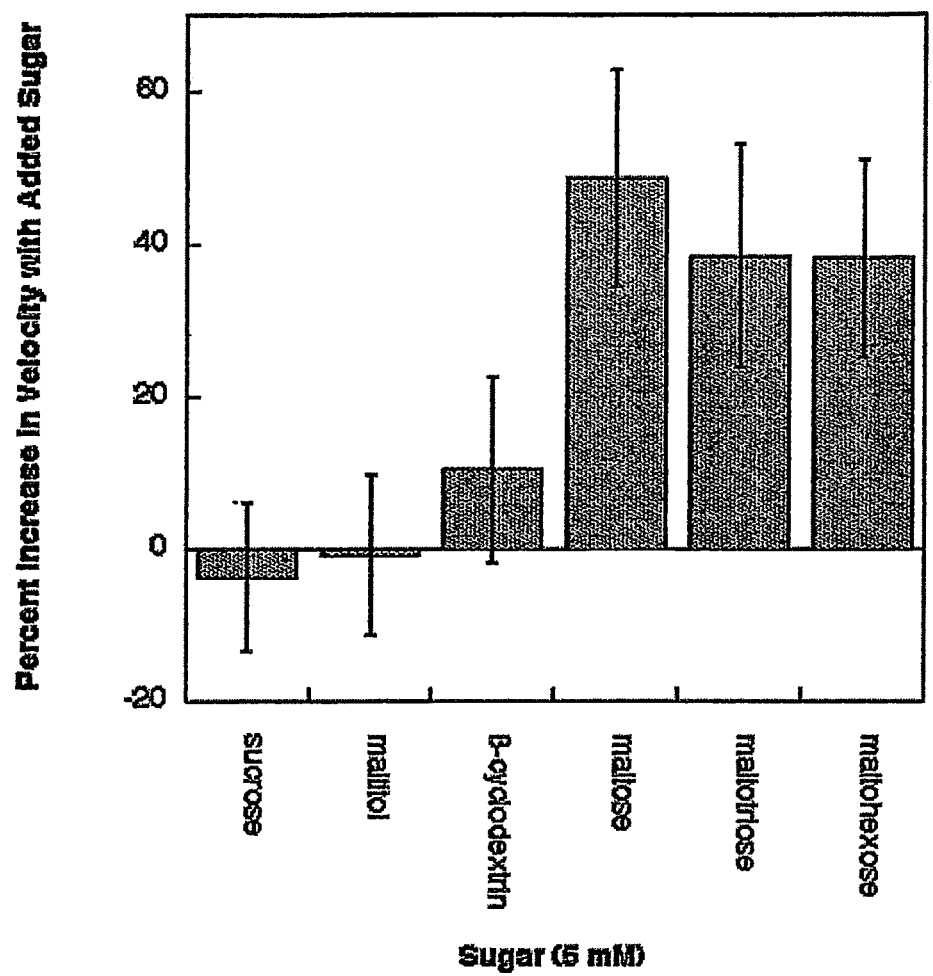

MOLECULAR SWITCHES AND METHODS FOR MAKING AND USING THE SAME

FIELD OF THE INVENTION

The invention relates to fusion molecules which function as molecular switches and to methods for making and using the same.

BACKGROUND OF THE INVENTION

Gene fusion technology, the fusion of two or more genes into a single gene, has been widely used as a tool in protein engineering, localization and purification. There are two conceptually different methods of making fusions. The simplest method, end-to-end fusions, has been used almost exclusively. The second method, insertional fusion, comprises the insertion of one gene into the middle of another gene. Insertions can result in a continuous domain being split into a discontinuous domain.

One of the first reports of successful insertion of one protein into another was a study by Ehrmann, et al., *Proc. Natl. Acad. Sci. USA* 87: 7574-8, who described the insertion of alkaline phosphatase (AP) into the *E. coli* outer membrane protein MalF, as a tool for studying membrane topology. High levels of alkaline phosphatase activity were obtained in the fusions despite the fact that alkaline phosphatase requires dimerization for activity. Since then, AP has been successfully inserted into a number of integral membrane proteins (see, e.g., Bibi and Beja, 1994, *J. Biol. Chem.* 269: 19910-5; Cosgriff and Pittard, 1997, *J. Bacteriol.* 179: 3317-23; Lacatena, et al., 1994, *Proc. Natl. Acad. Sci. USA* 91: 10521-5; Pi and Pittard, 1996, *J. Bacteriol.* 178: 2650-5; Pigeon and Silver, 1994, *Mol. Microbiol.* 14: 871-81).

Other proteins, including green fluorescent protein GFP (Biondi, et al., 1998, *Nucleic Acids Res.* 26: 4946-4952; Kratz, et al., 1999, *Proc. Natl. Acad. Sci. USA* 96: Siegel and Isacoff, 1997, *Neuron* 19: 73541; Siegel and Isacoff, 2000, *Methods Enzymol.* 327: 249-59), TEM1 β-lactamase (Betton, et al., 1997, *Nat. Biotechnology* 15: 1276-1279; Collinet, et al., 2000, *J. Biol. Chem.* 275: 17428-33; Ehrmann, et al., 1990, *Proc. Natl. Acad. Sci. USA* 87: 7574-8), thioredoxin (Lu, et al., 1995, *Biotechnology (NY)* 13: 366-72); dihydrofolate reductase (Collinet, et al., 2000, *J. Biol. Chem.* 275: 17428-33); FKBP12 (Tucker and Fields, *Nat. Biotechnol.* 19: 1042-6); estrogen receptor-α (Tucker and Fields, 2000, supra), and β-xylanase (Aÿ, et al., 1998, *Proc. Natl. Acad. Sci. USA* 95: 6613-6618); have been successfully inserted into other proteins. Such fusions at least partially retain the function of the inserted protein.

Doi, et al., 1999, *FEBS Letters* 453: 305-307, describe a fusion which comprises an insertion of the β-lactamase inhibiting protein (BLIP) polypeptide into a surface loop of the GFP protein. After several rounds of random mutagenesis, polypeptides were obtained which exhibited increased fluorescence upon bind of a ligand (β-lactamase) to the BLIP polypeptide.

More recently, yeast sensors for ligand binding were constructed by the insertion of FKBP12 and the estrogen receptor-α ligand-binding domain into a rationally chosen site in dihydrofolate reductase (DHFR) (see, e.g., Tucker and Fields, 2001, *Nature Biotechnology* 19: 1042-1046). The site of insertion was at residue 107, a site previously shown to be one tolerant of bisection (Pelletier, et al., 1998, *Proc. Natl. Acad. Sci. USA* 95: 12141-12146). The two fragments of DHFR divided at 107 were found to be unable to reassemble to form an active enzyme unless the fragments were fused to domains that dimerized (e.g., such as leucine zippers). Yeast expressing the FKBP12-DHFR or ERα-DHFR fusion proteins had an approximate two-fold increase in growth rate in the presence of their respective ligands (FK106 and estrogen) when DHFR activity limited growth. The fusion proteins were either fortuitously temperature sensitive (ERα-DHFR) or designed to be so by mutation (FKBP12-DHFR) in order that subtle changes in growth could be detected upon addition of the ligand.

Generally, methods for generating fusion molecules have not provided a systematic way to functionally couple protein domains.

SUMMARY OF THE INVENTION

The invention provides molecular switches which couple external signals, including, but not limited to, the presence, absence or level of molecules, ligands, metabolites, ions, and the like, the presence, absence, or level of chemical, optical or electrical conditions, to functionality. Preferably, the switches are fusion molecules comprising an insertion sequence and an acceptor sequence for receiving the insertion sequence, wherein the state of the insertion sequence is coupled to the state of the acceptor sequence. For example, the activity of the insertion sequence can be coupled to the activity/state of the acceptor sequence.

The "state" of a molecule can comprise its ability or latent ability to emit or absorb light, its ability or latent ability to change conformation, its ability or latent ability to bind to a ligand, to catalyze a substrate, transfer electrons, and the like. Preferably, molecular switches according to the invention are multistable, i.e., able to switch between at least two states. In one aspect, the fusion molecule is bistable, i.e., a state is either "ON" or "OFF", for example, able to emit light or not, able to bind or not, able to catalyze or not, able to transfer electrons or not, and so forth. In another aspect, the fusion molecule is able to switch between more than two states. For example, in response to a particular threshold state exhibited by an insertion sequence or acceptor sequence, the respective other sequence of the fusion may exhibit a range of states (e.g., a range of binding activity, a range of enzyme catalysis, etc.). Thus, rather than switching from "ON" or "OFF", the fusion molecule can exhibit a graded response to a stimulus. More generally, a molecular switch is one which generates a measurable change in state in response to a signal.

In one aspect, a molecular switch can comprise a plurality of fusion molecules responsive to a signal, which mediate a function in response to a change in state of at least a portion of the molecule. As above, preferably, this change of state occurs in response to a change in state of another portion of the molecule. While the states of individual fusion molecules in the population may be ON or OFF, the aggregate population of molecules may not be able to mediate the function unless a threshold number of molecules switch states. Thus, the "state" of the population of molecules may be somewhere in between ON or OFF, depending on the number of molecules which have switched states. This provides an ability to more precisely tune a molecular response to a signal by selecting for molecules which respond to a range of signals and modifying the population of fusion molecules to provide selected numbers of fusion molecules which respond to a narrow range or wider range of signal as desired.

In yet another aspect, the invention provides a fusion molecule comprising an insertion sequence and an acceptor sequence. The insertion sequence or the acceptor sequence localizes the fusion molecule intracellularly. Preferably, the fusion molecule is associated with a bio-effective molecule and intracellular localization is coupled to release of the bio-effective molecule from the fusion molecule.

The fusion molecules of the present invention also can comprise an insertion sequence and acceptor sequence, wherein either the insertion sequence or the acceptor sequence associates with a bio-effective molecule and disassociates from the bio-effective molecule when the respective other sequence of the fusion binds to a cellular marker of a pathological condition. In this aspect, the fusion molecule can be used to target bio-effective molecules, such as drugs, to cells having specific pathologies (e.g., cancer cells).

In still another aspect, the fusion molecule of the present invention is capable of switching from a non-toxic state to a toxic state. Either the insertion sequence or acceptor sequence may bind to a cellular marker of a pathology (e.g., such as a tumor antigen). Binding of the marker to the fusion protein switches the fusion protein from a toxic to a non-toxic state.

In a further aspect, the fusion molecule comprises a molecular switch for controlling a cellular pathway. The fusion molecule comprises an insertion sequence and an acceptor sequence and the states of the insertion sequence and acceptor sequence are coupled, such that the state of either the inserted sequence or the acceptor sequence modulates the activity or expression of a molecular pathway molecule in a cell. The invention can be used to modulate cellular responses using exogenous or endogenous binding molecules (e.g., ligands, small molecules, ions, metabolites, and the like) to transduce a desired signal.

In another aspect, the invention provides a fusion protein comprising an insertion sequence and an acceptor sequence, wherein either the insertion sequence or the acceptor sequence binds to a DNA molecule, and wherein DNA binding activity is coupled to the response of the respective other sequence of the fusion molecule to a signal. Preferably, the DNA to which the fusion molecule binds is a nucleic acid regulatory sequence for regulating the activity of another nucleic acid molecule (e.g., modulating transcription, translation, replication, recombination, supercoiling, etc., of the other nucleic acid molecule).

The invention also provides a sensor molecule comprising an insertion sequence and an acceptor sequence, wherein either the insertion sequence or acceptor sequence binds to a target molecule and wherein the respective other sequence generates a signal in response to binding. Preferably, the acceptor sequence comprises a deletion and/or duplication at the insertion site.

The invention also provides a combinatorial method for generating any of the molecular switches described above. Such an approach provides a means to systematically examine all or a substantial fraction of all possible fusions between insertion sequences and acceptor sequences, including ones in which deletions and tandem duplications occur at the insertion site. Preferably, given an acceptor sequence comprising a given number of monomers (e.g., bases, amino acids, etc.), at least about the same number of different fusions are generated, and more preferably, at least about twice this number of fusions are generated.

In one aspect, the method comprises domain insertion, i.e., randomly inserting an insertion sequence into an acceptor sequence and selecting for a fusion molecule in which the state of the insertion sequence is coupled to the state of the acceptor molecule. In another aspect, however, the method comprises generating first and second molecules with dimerization domains and selecting for molecules which dimerize in response to a condition, e.g., such as upon binding to a signaling molecule.

The invention also provides a method for assembling a modulatable fusion molecule, comprising: randomly inserting an insertion sequence into an acceptor sequence, wherein the insertion sequence and the acceptor sequence each comprise a state (e.g., such as an activity), thereby generating a fusion molecule, and selecting a fusion molecule wherein insertion couples a change in state of the insertion sequence to a change in the state of the acceptor sequence. In one aspect, an activity of the insertion sequence is modulated, preferably, in response to a change in a state of the acceptor sequence. In another aspect, the activity of the acceptor sequence is modulated, preferably in response to a change in the state of the insertion sequence. Insertion of the insertion sequence into the acceptor sequence, in some cases, may generate a new state (e.g., a new activity). The process of randomly inserting may generate a duplication or deletion at the insertion site, thereby increasing the numbers of types of fusions that can be examined.

The invention also provides a method for assembling a multistable fusion molecule which can switch between at least an active state and a less active state, an in some cases, an inactive state. The method comprises randomly inserting an insertion sequence into an acceptor sequence, thereby generating a fusion molecule, wherein either the insertion sequence or the acceptor sequence comprises an activity; and wherein the respective other sequence is responsive to a signal. A fusion molecule is selected in which activity is coupled to the signal such that the fusion molecule switches state in response to the signal. The signal can comprise binding of a ligand, a change in conformation, a chemical, optical, electrical, magnetic signal, the absence of such conditions, and the like. In one aspect, the method comprises randomly inserting an insertion sequence responsive to a signal into an acceptor sequence comprising an activity, thereby generating a fusion molecule, and selecting for a fusion molecule wherein the activity of the acceptor sequence is responsive to the signal.

Preferably, the insertion sequence and acceptor sequence comprise polypeptides and in one aspect, the step of randomly inserting the insertion molecule into the acceptor molecule comprises obtaining a first nucleic acid fragment encoding the insertion polypeptide and a second nucleic acid fragment encoding the acceptor polypeptide and randomly inserting the first nucleic acid fragment into the second nucleic acid fragment. The method may further comprise the step of digesting the second nucleic acid with a nuclease such as DNase I, S1 nuclease, mung bean nuclease, a restriction endonuclease, or a combination thereof, shearing the second nucleic acid (e.g., mechanically), or otherwise treating the second nucleic acid to introduce breaks (e.g., exposing the nucleic acid to chemical agents and/or radiation). The nucleic acid sequence encoding the insertion sequence may also be digested, sheared, or otherwise treated, to generate random fragments of the insertion sequence. Preferably, such fragments are inserted at random into the sites of breaks in the nucleic acid sequence encoding the acceptor molecule caused by the nuclease digestion.

The step of insertion can be repeated a plurality of times with a plurality of first and second nucleic acid molecules, either sequentially or simultaneously, to generate a library of acceptor polypeptides comprising randomly inserted insertion polypeptide sequences. The library can be used to identify fusion polypeptides wherein the states of the insertion polypeptide and acceptor polypeptide are coupled, and preferably, responsive to a signal.

In one aspect, the library comprises members comprising insertions with deletions at the insertion site, insertions with tandem duplications at the insertion site, and insertions with neither duplications nor deletions.

The invention also provides expression vectors for expression of the fusion molecules as well as host cells for expressing the fusion molecules. Host cells can include microorganisms, animal cells, and plant cells. In one aspect, fusion molecules are expressed in one or more cells of a transgenic organism. Fusion molecules according to the invention can thus be used to provide a conditional knockout or knock-in of a biomolecule in a cell.

The invention further provides a method for modulating a cellular activity comprising providing any of the fusion molecules described above, wherein a change in state of at least the insertion sequence or the acceptor sequence modulates a cellular activity, and wherein the change in state which modulates the cellular activity is coupled to a change in state of the respective other portion of the fusion molecule. The cellular activity is modulated by changing the state of the respective other portion of the fusion molecule.

In another aspect, the invention provides a method for delivering a bio-effective molecule to a cell. The method comprises providing a fusion molecule associated with a bio-effective molecule to the cell, the fusion molecule comprising an insertion sequence and an acceptor sequence. Preferably, either the insertion sequence or the acceptor sequence binds to a cellular marker of a pathological condition and upon binding to the marker, the fusion molecule dissociates from the bio-effective molecule, thereby delivering the molecule to the cell.

In still another aspect, the invention provides a method for delivering a bio-effective molecule intracellularly. The method comprises providing a fusion molecule associated with a bio-effective molecule to the cell, the fusion molecule comprising an insertion sequence and an acceptor sequence. Either the insertion sequence or acceptor sequence comprises a transport sequence for transporting the fusion molecule intracellularly. Preferably, release of the bio-effective molecule from the fusion molecule is coupled to transport of the fusion molecule intracellularly. Preferably, either the inserted sequence or the acceptor sequence is capable of binding to a biomolecule and binding of the fusion molecule with the biomolecule transports the fusion molecule intracellularly and disassociates the bio-effective molecule from the fusion molecule.

The invention also provides a method for modulating a molecular pathway in a cell. The method comprises providing a fusion molecule to the cell, the fusion molecule comprising an insertion sequence and an acceptor sequence. The states of the insertion sequence and acceptor sequence are coupled and responsive to a signal, and the state of either the insertion sequence or the acceptor sequence modulates the activity or expression of a molecular pathway molecule in the cell. Upon exposure of the fusion molecule to the signal, the fusion molecule is thus able to modulate the molecular pathway.

The invention additionally provides a method for controlling the activity of a nucleic acid regulatory sequence. The method comprises providing a fusion molecule which comprises an insertion sequence and an acceptor sequence, wherein either the insertion sequence or the acceptor sequence responds to a signal, and wherein the respective other sequence of the fusion molecule binds to the nucleic acid regulatory sequence when the signal is responded to. Exposing the fusion molecule to the signal modulates the activity of the nucleic acid regulatory sequence. Types of activities regulated include, but are not limited to, modulating transcription, translation, replication, recombination, or supercoiling.

The invention also provides a method for generating a conditional heterodimer, comprising: providing a plurality of randomly bisected molecules; each bisected molecule comprising a first portion and a second portion, wherein the first and second portions are fused to first and second dimerization domains respectively, and wherein a function of the bisected molecule is altered by bisection. By selecting for restoration of function of a bisected molecule in response to a signal, a conditional heterodimer may be obtained.

In one aspect, a conditional heterodimer is used to conditionally provide an activity to a cell. Preferably, the dimerization is mediated by a signal, such as binding of drug to the dimerization domain such that the activity can be triggered by administering a drug to the cell.

BRIEF DESCRIPTION OF THE FIGURES

The objects and features of the invention can be better understood with reference to the following detailed description and accompanying drawings.

FIGS. 1A-C are schematic diagrams illustrating strategies for generating molecular switches according to the invention. FIG. 1A shows a domain insertion strategy according to one aspect of the invention. FIG. 1B shows conditional heterodimers according to another aspect of the invention. FIG. 1C shows a strategy for generating an enzyme:binding protein hybrid according to one aspect of the invention. As shown in FIG. 1C, catalytic activity of an enzyme domain of the fusion molecule is coupled to binding of the fusion molecule to a signaling protein (protein B).

FIGS. 2A-D show cloning steps in generating libraries of fusion molecules according to one aspect of the invention. FIG. 2A (SEQ ID NOS 29-38 respectively in order of appearance) shows preparation of a nucleic acid encoding an insertion sequence (e.g., β-lactamase) for subsequent cloning steps. FIG. 2B shows random insertion of the insertion sequence into acceptor sequences digested with a nuclease. FIG. 2C shows a variation of the insertion method shown in 2B which comprises incremental truncation. FIG. 2D is a flow chart illustrating selection of active fusions according to one aspect of the invention.

FIGS. 3A-G illustrate methods of using molecular switches according to aspects of the invention. FIG. 3A shows regulation of gene transcription using a fusion molecule according to one aspect of the invention (SEQ ID NOS 39-41 respectively in order of appearance). FIG. 3B shows modulation of a cell signaling pathway according to another aspect of the invention. FIG. 3C shows drug delivery mediated by a fusion molecule to a cell expressing a marker of a pathology. FIG. 3D shows the use of fusion molecules for drug transport to an intracellular compartment. FIG. 3E shows delivery of a conditionally toxic fusion molecule to a cell. FIG. 3F shows the use of a fusion molecule for metabolic engineering. FIG. 3G shows a fusion molecule according to one aspect of the invention which functions as a biosensor.

FIGS. 5A-C show a strategy for engineering a switch molecule by generating a conditional heterodimer. FIG. 5A shows bisecting a polypeptide whose function is to be controlled into two fragments that cannot functionally associate by themselves. FIG. 5B shows selection of molecules which functionally associate when fused to dimerization domains. FIG. 5C shows dimerization which occurs in response to a signal according to one aspect of the invention.

FIG. 6A shows a method for generating libraries of such molecules. FIG. 6B shows the addition of dimerization domains.

FIG. 8 shows the effect of sugars on a T164-165 β-lactamase: maltose binding protein (MBP) fusion's hydrolysis of nitrocefin. The fusion comprises an insertion of β-lactamase amino acid sequences into an MBP acceptor polypeptide with a tandem duplication of amino acids 164-165 of MBP at the insertion site. The velocity of nitrocefin hydrolysis with 150 μM nitrocefin and 5 mM of the indicated sugars was compared to the velocity without any sugar. Sugars known not to bind wildtype MBP (sucrose) and those that bind to MBP, but do not introduce a confromational change (maltitol and β-cyclodextrin) did not have a significant effect on nitrocefin hydrolysis. All sugars known to bind to wildtype MBP and induce a conformational change (maltose, maltotriose and maltohexose) increase the rate of hydrolysis by approximately 40%.

DETAILED DESCRIPTION

Figure 1A:
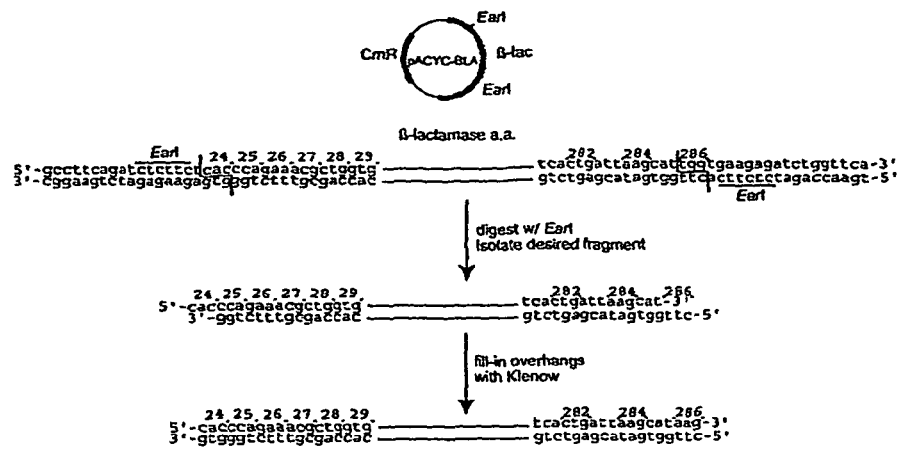

The invention provides molecular switches which couple external signals to functionality and to methods of making and using the same. The switches according to the invention can be used, for example, to regulate gene transcription, target drug delivery to specific cells, transport drugs intracellularly, control drug release, provide conditionally active proteins, perform metabolic engineering, and modulate cell signaling pathways. Libraries comprising the switches and expression vectors and host cells for expressing the switches are also provided.

Definitions

The following definitions are provided for specific terms which are used in the following written description.

As used herein, a "molecular switch" refers to a molecule which generates a measurable change in state in response to a signal. In one aspect, a molecular switch is capable of switching from at least one state to at least one other state in response to the signal. Preferably, when a portion of the molecule responds to the signal, the portion become activated (i.e., turns "ON") or inactivated (i.e., turns "OFF"). In response to this change in state, the state of another portion of the fusion molecule will change (e.g., turn ON or OFF). In one aspect, a switch molecule turns ON one portion of the molecule when another portion is turned OFF. In another aspect, the switch turns ON one portion of the molecule, when the other portion is turned ON. In still another aspect, the switch molecule turns OFF one portion of the molecule when the other portion is turned ON. In a further aspect, the switch molecule turns OFF, when the other portion is turned OFF. In some aspects of the invention, a molecular switch exists in more than two states, i.e., not simply ON or OFF. For example, a portion of the fusion molecule may display a series of states (e.g., responding to different levels of signal), while another portion of the fusion molecule responds at each state, with a change in one or more states. A molecular switch also can comprise a plurality of fusion molecules responsive to a signal and which mediate a function by changing the state of at least a portion of the molecule (preferably, in response to a change in state of another portion of the molecule). While the states of individual fusion molecules in the population may be ON or OFF, the aggregate population of molecules may not be able to mediate the function unless a threshold number of molecules switch states. Thus, the "state" of the population of molecules may be somewhere in between ON or OFF depending on the number of molecules which have switched states. In one aspect, a molecular switch comprises a heterogeneous population of fusion molecules comprising members which switch states upon exposure to different levels of signal. In other aspects of the invention, however, the state of a single molecule may be somewhere in between ON or OFF. For example, a molecule may comprise a given level of activity, ability to bind, etc., in one state which is switched to another given level of activity, ability to bind, etc., in another state (i.e., an activity, ability to bind, etc., measurably higher or lower than the activity, ability to bind, etc., observed in previous state).

As used herein, a "state" refers to a condition of being. For example, a "state of a molecule" or a "state of a portion of a molecule" can be a conformation, binding affinity, or activity (e.g., including, but not limited to, ability to catalyze a substrate; ability to emit light, transfer electrons, transport or localize a molecule, modulating transcription, translation, replication, supercoiling, and the like).

As defined herein, a molecule, or portion thereof, whose state is "activated" refers to a molecule or portion thereof which performs an activity, such as catalyzing a substrate, emitting light, transferring electrons, catalyzing a substrate, transporting or localizing a molecule; changes conformation; binds to a molecule, etc.

As defined herein, a molecule, or portion thereof, whose state is "inactivated" refers to a molecule or portion thereof which is, at least temporarily, unable to perform an activity or exist in a particular state (e.g., bind to a molecule, change conformation).

As used herein, "coupled" refers to a state which is dependent on another state such that a measurable change in the other state is observed. As used herein, "measurable" refers to a that is significantly different from a baseline or a previously existing state as determined in a suitable assay using routine statistical methods (e.g., setting $p<0.05$).

As used herein, "a signal" refers to a molecule or condition that causes a reaction. Signals include, but are not limited to, the presence, absence, or level, of molecules (nucleic acids, proteins, peptides, organic molecules, small molecules), ligands, metabolites, ions, organelles, cell membranes, cells, organisms (e.g., pathogens), and the like; as well as the presence, absence, or level of chemical, optical, magnetic, or electrical conditions, and can include conditions such as degrees of temperature and/or pressure. A chemical condition can include a level of ions, e.g., pH.

As used herein, "responsive to a signal" refers to a molecule whose state is coupled to the presence, absence, or level of the signal.

As used herein, "an insertion sequence" refers to a polymeric sequence which is contained within another polymeric sequence (e.g., an "acceptor sequence") and which conditionally alters the state of the other polymeric sequence. An insertion sequence or acceptor sequence can comprise a polypeptide sequence, nucleic acid sequence (DNA sequence, aptamer sequence, RNA sequence, ribozyme sequence, hybrid sequence, modified or analogous nucleic acid sequence, etc), carbohydrate sequence, and the like.

As used herein, "multistable" refers to a fusion molecule which is capable of existing in at least two states.

As used herein, "bistable" refers to a fusion molecule capable of existing in two states.

As used herein, "range of states" refers to a series of states in which a fusion molecule can exist. For example, a range of states can comprise a range of binding activities, a range of light-emitting activities, a range of catalysis efficiencies, and the like.

As used herein, "a change in state" refers to a measurable difference in a state of being of a molecule, as determined by an assay appropriate for that state.

As used herein, "a graded response" refers to the ability of a fusion molecule to switch to a series of states in response a particular threshold signal.

As used herein, "modulates" or "modulated" refers to a measurable change in a state or activity or function. Preferably, where an activity is being described, "modulated" refers to an at least 2-fold, at least 5-fold, at least 10-fold, at least 20-fold or higher, increase or decrease in activity, or an at least 10%, at least 20%, at least 30%, at least 40% or at least 50% increase or decrease in activity. However, more generally, any difference which is measurable and statistically different from a baseline is encompassed within the term "modulated".

As used herein, a "less active state" is a state which is at least about 2-fold less active compared to a given reference state as measured using an assay suitable for measuring that state, or about at least 10%, at least about 20%, at least about 30%, at least about 40%, at least about 50%, at least about 60%, at least about 70%, at least about 80%, at least about 90% or at least about 100% less active. More generally, any decrease which is measurable and statistically different from baseline is encompassed within the term "less active state".

As used herein, a "less toxic state" refers to a measurable increase in the $LD_{50}$ (i.e., lethal dose which has a 50% probability of causing death) or $LC_{50}$ (i.e., lethal concentration which has a 50% probability of causing death). Preferably, a less toxic state is one which is associated with an at least about 10% increase, at least about 20%, at least about 30%, at least about 40%, at least about 50%, at least about 60%, at least about 70%, at least about 80%, at least about 90% or at least about 100% increase in $LD_{50}$ or $LC_{50}$.

As used herein, "a bio-effective molecule" refers to bioactive molecule which can have an affect on the physiology of a cell or which can be used to image a cell. In one aspect, a "bio-effective molecule" is a pharmaceutical agent or drug or other material that has a therapeutic effect on the cell.

As used herein, "a cellular marker of a pathological condition" refers to a molecule which is associated with a cell, e.g., intracellularly or extracellularly, and whose presence or level correlates with the presence of the disease, i.e., the marker is found in, or on cells, or is secreted by cells, exhibiting the pathology at levels which are significantly different than observed for cells not exhibiting the pathology.

As used herein, "a molecular pathway molecule" refers to a molecule whose activity and/or expression affects the activity and/or expression of at least two other molecules. Preferably, a molecular pathway molecule is a molecule involved in a metabolic or signal transduction pathway. A pathway molecule can comprise a protein, polypeptide, peptide, small molecule, ion, cofactor, organic and inorganic molecule, and the like.

As used herein, "modulating a molecular pathway" refers to a change in the expression and/or activity of at least one pathway molecule.

As used herein, "at an insertion site" of a nucleic acid molecule refers to from about 1 to 21 nucleotides immediately flanking the insertion site.

As used herein, "randomly inserting" refers to insertion at non-selected sites in a polymeric sequence. In one aspect, "random insertion" refers to insertion that occurs in a substantially non-biased fashion, i.e., there is a substantially equal probability of inserting between members of any pairs of monomers (e.g., nucleotides or amino acids) in an acceptor molecule comprising a given number of monomeric sequences. However, in another aspect, random insertion has some degree of bias, e.g., there is a greater than equal probability of inserting at different sites. Minimally, the probability of insertion at a site in an acceptor sequence is greater than zero but less than one.

As used herein, "a new activity" refers to an activity which is not found in either donor or acceptor sequences. Generally, fusion molecules according to the invention comprise a new activity in that the activity of the acceptor sequence or insertion sequence is newly coupled to the state of the respective other portion of the sequence. An insertion or acceptor sequence also may comprise a catalytic site which responds to (e.g., catalyzes) a substrate provided in the form of the respective other portion of the fusion molecule, thereby producing a fusion molecule which comprises an activity present in neither the original catalytic site or the substrate (e.g., such as the ability to self-cleave in the presence of a signal).

As used herein, "a nuclear regulatory sequence refers to" a nucleic acid sequence which is capable of modulating the activity of another nucleic acid in cis or in trans. Types of activities regulated include, but are not limited to, modulating transcription, translation, replication, recombination, or supercoiling. A nucleic acid regulatory sequence can include promoter elements, operator elements, repressor elements, enhancer sequences, ribosome binding sites, IRES sequences, origins of replication, recombination hotspots, topoisomerase binding sequences, and the like.

As used herein, "altered by bisection" refers to a change in state upon fragmenting a polypeptide into two pieces. The term "bisection" does not imply that the polypeptide is divided into fragments of equal size; rather fragments can be generated by cleaving anywhere along the length of the primary sequence of the amino acid.

As used herein, "selecting for restoration of function or state" refers to selection for restoration of a function or state which is sufficiently similar to that of the original function under assay conditions suitable for evaluating the function or state. As used herein, "sufficiently similar" refers to a state that can achieve the original function in an effective manner For example, when the function/state is binding, restoration of function/state can be evaluated by generating Scatchard plots and/or determining $K_d$. When the function/state is the ability of a molecule to generate light, restoration can be measured spectrophotometrically, for example.

As used herein, a "modification" of a polypeptide refers to an addition, substitution or deletion of one or more amino acids in a polypeptide which does not substantially alter the state of the polypeptide. For example, where a state is an activity of a polypeptide, a modification results in no more than a 10% decrease or increase in the activity of the polypeptide, and preferably no more than a 5% decrease or increase in the activity of the polypeptide.

Fusion Molecules

Domain Insertion

Figure 1B:
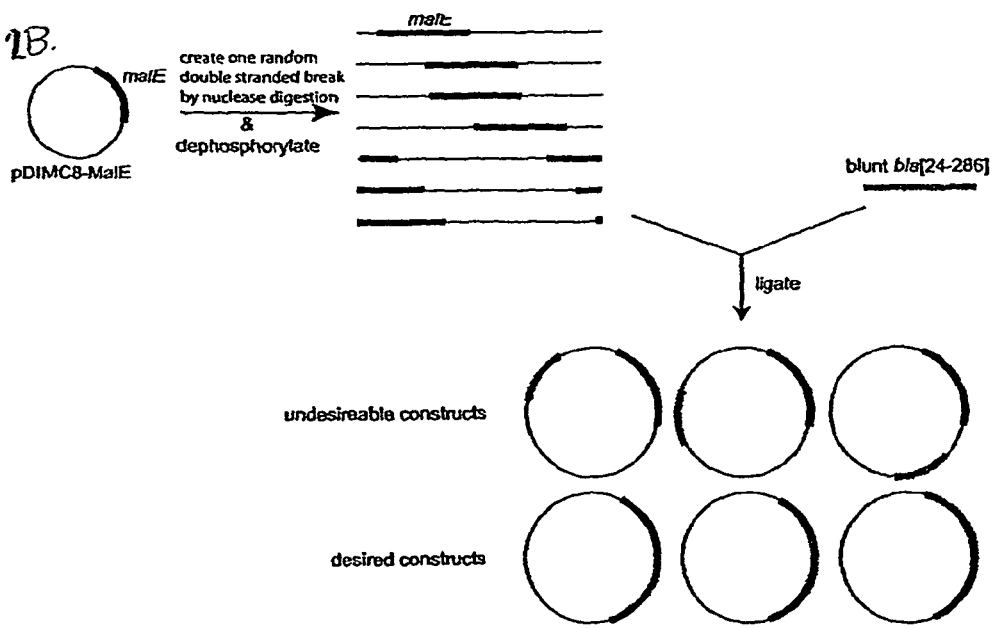

In one aspect, a fusion molecule is provided which comprises an insertion sequence and an acceptor sequence which contains the insertion sequence (see, FIG. 1B). Preferably, the insertion sequence and acceptor sequence are polymeric molecules, e.g., such as polypeptides or nucleic acids. More preferably, both the insertion sequence and acceptor sequence are capable of existing in at least two states and the state of the insertion sequence is coupled to the state of the acceptor sequence upon fusion, such that a change in state in either the insertion sequence or acceptor sequence will result in a change in state of respective other portion of the fusion. A "state" can be a conformation; binding affinity; ability or latent ability to catalyze a substrate; ability or latent ability to emit light; ability or latent ability to transfer electrons; ability or latent ability to withstand degradation (e.g., by a protease or nuclease); to modulate transcription; ability or latent ability to modulate translation; ability or latent ability to modulate replication; ability or latent ability to initiate or mediate recombination or supercoiling; or otherwise perform a function; and the like.

Preferably, the change in state is triggered by a signal to which the fusion molecule is exposed, e.g., such as the presence, absence, or amount of a small molecule, ligand, metabolite, ion, organelle, cell membrane, cell, organism (e.g., such as a pathogen), temperature change, pressure change, and the like, to which the fusion molecule binds; a change in a condition, such as pH, or a change in the chemical, optical, electrical, or magnetic environment of the fusion molecule. In one aspect, a fusion molecule functions as an ON/OFF switch in response to a signal (e.g., changing from one state to another). For example, when an insertion sequence or acceptor sequence of the fusion molecule binds to a ligand, the respective other half of the fusion may change state (e.g., change conformation, bind to a molecule, release a molecule to which it is bound, catalyze a substrate or stop catalyzing a substrate, emit light or stop emitting light, transfer electrons or stop transferring electrons, activate or inhibit transcription, translation, replication, etc.).

However, fusion molecules according to the invention also can be used to generate graded responses. In this scenario, a fusion molecule can switch from a series of states (e.g., more than two different types of conformations, levels of activity, degrees of binding, levels of light transmission, electron transfer, transcription, translation, replication, etc). Preferably, the difference in state is one which can be distinguished readily from other states (e.g., there is a significant measurable difference between one state and any other state, as determined using assays appropriate for measuring that state).

More generally, a molecular switch is one which generates a measurable change in state in response to a signal. For example, a molecular switch can comprise a plurality of fusion molecules each responsive to a signal and for mediating a function in response to a change in state of at least a portion of the molecule. As above, preferably, this change of state occurs in response to a change in state of another portion of the molecule. While the states of individual fusion molecules in the population may be ON or OFF, the aggregate population of molecules may not be able to mediate the function unless a threshold number of molecules switch states. Thus, the "state" of the population of molecules may be somewhere in between ON or OFF, depending on the number of molecules which have switched states. This provides an ability to more precisely tune a molecular response to a signal by selecting for molecules which respond to a range of signals and modifying the population of fusion molecules to provide selected numbers of fusion molecules, providing an aggregate switch which respond to a narrow range or wider range of signal as desired. Thus, in one aspect, a heterogeneous population of fusion molecules is provided comprising members which respond to different levels or ranges of signals. Individual fusion molecules also may exist in states intermediate between ON or OFF; e.g., having a given level of activity, ability to bind to a molecule in one state and a measurably higher or lower level of activity, ability to bind, etc., in a different state.

Insertion Sequences

The size of the insertion will vary depending on the size of an insertion sequence required to confer a particular state on the insertion sequence without significantly disrupting the ability of the acceptor molecule into which it is inserted to change state. Preferably, the affect of the insertion is to couple the change in state of the acceptor molecule to a change in state of the insertion molecule or visa versa.

Generally, for polypeptide insertions, the size of the insertion sequence can range from about two amino acids to at least about 120 amino acids. In one aspect, the insertion comprises a domain sequence with a known characterized activity (e.g., a portion of a protein in which bioactivity resides); however, in other aspects, the insertion sequence comprises an entire protein sequence.

In one aspect, the insertion sequence is a polypeptide whose folded conformation is such that the N- and C-termini are "on the same face" of a fusion molecule comprising the insertion sequence.

Acceptor Sequences

Generally, there are no constraints on the size or type of acceptor sequence which can be used. However, in one aspect, an acceptor sequence is a polypeptide whose state resides in a discontinuous domain of a protein (e.g., the amino acids involved in conferring the state/activity of the acceptor sequence are not necessarily contiguous in the primary polypeptide sequence) (see, e.g., as described in Russell and Ponting, 1998, *Curr. Opin. Struct. Biol.* 8: 364-371, and Jones, et al., 1998, *Protein Sci.* 7: 233-42).

Suitable polypeptides for acceptor molecules can be identified using domain assignment algorithms such as are known in the art (e.g., such as the PUU, DETECTIVE, DOMAK, and DomainParser, programs). For example, a consensus approach may be used as described in Jones, et al., 1998, supra. Information also can be obtained from a number of molecular modeling databases such as the NIH Molecular Modelling Homepage, accessible at http://cmm.info.nih.gov/modeling/pdb_at_a_glance.html; or the 3Dee Database described by Dengler, et al., 2001, *Proteins* 42(3): 33244. However, the most important criteria used for selecting a sequence is its function, e.g., the desired state parameters of the fusion molecule.

However, in a further aspect, no pre-screening is done and an acceptor sequence is selected simply on the basis of a desired activity. The power of the methods according to the invention is that they rely on combinatorial screening to identify any, and preferably, all, combinations of insertions that produce a desired coupling in states of acceptor and donor molecules.

Domain Sequences

In one aspect, the insertion sequence or acceptor sequence comprises a "domain" sequence having a known state. Domains can be minimal sequences, such as are known in the art, which are associated with a particular known state or can be an entire protein comprising the domain or a functional fragment thereof.

Minimal domain sequences can be defined by site-directed mutagenesis of a sequence having a desired state to determine the minimum amino acids necessary to confer the existence of the state under the appropriate conditions (e.g., such as a minimal binding site sequence or a minimum sequence necessary for catalysis, light emission, etc.). As discussed above, minimal domain sequences also can be defined virtually, using algorithms to identify consensus sequences or areas of likely protein folding. Once a domain sequence has been identified, it can be modified to include additional sequences, as well as insertions, deletions, and substitutions of amino acids so long as they do not substantially affect the state of the domain sequence. While domain sequences can be obtained using nucleic acids encoding appropriate fragments of polypeptides, they also can be synthesized, for example, based on a predicted consensus sequence for a class of molecules which is associated with a particular state. However, as discussed above, in some cases it may be desirable to provide the domain sequence in the form of a native protein comprising the domain.

Suitable domain sequences include extracellular domains which are portions of proteins normally found outside of the plasma membrane of a cell. Preferably, such domains bind to bio-effective molecules. For example, an extracellular domain can include the extracytoplasmic portion of a transmembrane protein, a secreted protein, a cell surface targeting protein, a cell adhesion molecule, and the like. In one aspect, an extracellular domain is a clustering domain, which, upon activation by a bio-effective molecule will dimerize or oligomerize with other molecules comprising extracellular domains.

Intracellular domains also can serve as insertion sequences or acceptor sequences. As used herein, "an intracellular domain" refers to a portion of a protein which generally resides inside of a cell with respect to the cellular membrane. In one aspect, an intracellular domain is one which transduces an extracellular signal into an intracellular response. For example, an intracellular domain can comprise a proliferation domain which signals a cell to enter mitosis (e.g., such as domains from Jak kinase polypeptides, Il-2 receptor β and/or gamma chains, and the like). Other transducer sequences include sequences from the zeta chain of the T cell receptor or any of its homologs (e.g., the eta chain, Fc epsilon R1-gamma and -62 chains, MB1 chain, B29 chain, and the like), CD3 polypeptides (gamma, beta and epsilon), syk family tyrosine kinases (Syk, ZAP 70, and the like), and src family tyrosine kinases (Lck, Fyn, Lyn, and the like).

A transmembrane domain also can be used as an insertion sequence or acceptor sequence. Preferably, a transmembrane domain is able to cross the plasma membrane and can, optionally, transduce an extracellular signal into an intracellular response. Preferred transmembrane sequences include, but are not limited to, sequences derived from CD8, ICAM-2, IL-8R, CD4, LFA-1, and the like.

Transmembrane sequences also can include GPI anchors, e.g., such as the DAF sequence (PNKGSGTTSGTTRLLS-GHTCFTLTGLLGTLVTMGLLT) (see, e.g., Homans, et al., 1988, Nature 333(6170): 269-72; Moran, et al., 1991, J. Biol. Chem. 266: 1250); myristoylation sequences (e.g., such as the src sequence MGSSKSKPKDPSQR) (see Cross, et al., 1984, Mol. Cell Biol. 4(9): 1834; Spencer, et al., 1993, Science 262: 1019-1024); and palmitoylation sequences (e.g., such as the GRK6 sequence LLQRLFSRQDCCGNCSDSEEELPTR).

Either the insertion sequence or the acceptor sequence can be a localization sequence for localizing a molecule comprising the sequence intracellularly. In one aspect, the localization sequence is a nuclear localization sequence. Generally, a nuclear localization sequence is a short, basic sequence that serves to direct a polypeptide in which it occurs to a cell's nucleus (Laskey, 1986, Ann. Rev. Cell Biol. 2:367-390; Bonnerot, et al., 1987, Proc. Natl. Acad. Sci. USA 84: 6795-6799; Galileo, et al., 1990, Proc. Natl. Acad. Sci. USA 87: 458-462, 1990). Suitable nuclear localization sequences include, but are not limited to, the SV40 (monkey virus) large T Antigen sequence (PKKKKKV) (see, e.g., Kalderon, 1984, et al., Cell 39: 499-509); the human retinoic acid receptor nuclear localization signal (ARRRRP); NF κβ p50 sequence (EEVQRKRQKL) (Ghosh et al., 1990, Cell 62: 1019); the NF κB p65 sequence (EEKRKRTYE) (Nolan et al., 1991, Cell 64: 961); and nucleoplasmin (Ala Val Lys Arg PAATLKK-AGQAKKKKLD) (Dingwall, et al., 1982, Cell 30:449-458).

The localization sequence can comprise a signaling sequence for inserting at least a portion of the fusion molecule into the cell membrane. Suitable signal sequences include residues 1-26 of the IL-2 receptor beta-chain (see, Hatakeyama et al., 1989, Science 244: 551; von Heijne et al, 1988, Eur. J. Biochem. 174: 671); residues 1-27 of the insulin receptor β chain (see, Hatakeyama, et al., 1989, supra); residues 1-32 of CD8 (Nakauchi, et al., 1985, PNAS USA 82: 5126) and residues 1-21 of ICAM-2 (Staunton, et al., 1989, Nature (London) 339: 61).

The localization sequence also can comprise a lysozomal targeting sequence, including, for example, a lysosomal degradation sequence such as Lamp-2 (KFERQ) (see, e.g., Dice, 1992, Ann. N.Y. Acad. Sci. 674: 58); a lysosomal membrane sequence from Lamp-1 (MLIPIAGFFALAGLVLIVLIAYLI-GRKRSHAGYOTI) (e.g., Uthayakumar, et al., 1995, Cell. Mol. Biol. Res. 41: 405) or Lamp-2 (LVPIAVGAALAGV-LILVLLAYFIGLKHHHAGYEQF) (e.g., Konecki et al., 1994, Biochem. Biophys. Res. Comm. 205: 1-5).

Alternatively, the localization sequence can comprise a mitochondrial localization sequence, including, but not limited to: mitochondrial matrix sequences, such as the MLRTSSLFTRRVQPSLFSRNILRLQST of yeast alcohol dehydrogenase III (Schatz, 1987, Eur. J. Biochem. 165:1-6); mitochondrial inner membrane sequences, such as the MLSLRQSIRFFKPATRTLCSSRYLL sequence of yeast cytochrome c oxidase subunit IV (Schatz, 1987, supra); mitochondrial intermembrane space sequences, such as the MFSMLSKRWAQRTLSKSFYSTAT-GAASKSGKLTQKLVTAGVAAAGITASTLL YADSLTAE-AMTA sequence of yeast cytochrome c1 (Schatz, 1987, supra); or mitochondrial outer membrane sequences, such as the MKSFITRNKTAILATVAATG-TAIGAYYYYNQLQQQQQRGKK sequence of yeast 70 kD outer membrane protein (see, e.g., Schatz, supra).

Other suitable localization sequences include endoplasmic reticulum localizing sequences, such as KDEL from calreticulin (e.g., Pelham, 1992, Royal Society London Transactions B: 1-10) or the adenovirus E3/19K protein sequence LYLSRRSFIDEKKMP (Jackson et al., 1990, EMBO J. 9: 3153); and peroxisome targeting sequences, such as the peroxisome matrix sequence (SKL) from Luciferase (Keller et al., 1987, Proc. Natl. Acad. Sci. USA 4: 3264).

In another aspect, the insertion sequence or acceptor sequence comprises a secretory signal sequence capable of effecting the secretion of the fusion molecule from a cell (see, e.g., Silhavy, et al., 1985, *Microbiol. Rev.* 49: 398-418). This may be useful for generating a switch molecule which can affect the activity of a cell other than a host cell in which it is expressed. Suitable secretory sequences, include, but are not limited to the MYRMQLLSCIALSLALVTNS sequence of IL-2 (Villinger, et al., 1995, *J. Immunol.* 155: 3946); the MATGSRTSLLLAFGLLCLPWLQEGSAFPT sequence of growth hormone (Roskam et al., 1979, *Nucleic Acids Res.* 7: 30); the MALWMRLLPLLALLALWGPDPAAAFVN sequence of preproinsulin (Bell, et al., 1980, *Nature* 284: 26); the influenza HA protein sequence, MKAKLLVL-LYAFVAGDQI (Sekiwawa, et al., *Proc. Natl. Acad. Sci. USA* 80: 3563); or the signal leader sequence from the secreted cytokine IL4, MGLTSQLLPPLFFLLACAGNFVHG.

In a further aspect, the insertion sequence or acceptor sequence comprises a domain for binding a nucleic acid. The domain can comprise a DNA binding polypeptide or active fragment thereof from a prokaryote or eukaryote. For example, the domain can comprise a polypeptide sequence from a prokaryotic DNA binding protein such as gp 32; a domain from a viral protein, such as the papilloma virus E2 protein; or a domain from a eukaryotic protein, such as p53, Jun, Fos, GCN4, or GAL4. Novel DNA binding proteins also can be generated by mutagenic techniques (see, e.g., as described in U.S. Pat. No. 5,198,346).

The insertion sequence or acceptor sequence also can comprise the $Ca^{2+}$ binding domain of a Ca+ binding protein such as calmodulin, parvalbumin, troponin, annexin, and myosin or the ligand domain of a binding protein such as avidin, concanavalin A, ferritin, fibronectin, an immunoglobulin, a T Cell Receptor, an MHC Class I or Class II molecule, a lipid binding protein, a metal binding protein, a chaperone, a G-Protein Coupled Receptor, and the like.

In addition, the insertion or acceptor sequence can comprise the transport domain of a transport protein such as hemerythrin, hemocyanin, hemoglobin, myoglobin, transferrin, lactoferrin, ovotransferrin, maltose binding protein and transthyretrin.

In another aspect, the insertion or acceptor sequence can comprise the active domain of a blood coagulation protein (e.g., a domain which mediates blood clotting). Exemplary blood clotting proteins include, but are not limited to: decorsin, factor IX, factor X, kallikrein, plasmin/plasminogen, protein C, thrombin/prothrombin, and tissue-type plasminogen activator.

In still another aspect, the insertion or acceptor sequence can comprise the active domain of an electron transport protein (e.g., a domain which confers electron transport activity on a protein). Electron transport proteins include, but are not limited to, amicyanin, azurin, a cytochrome protein, ferrodoxin, flavodoxin, glutaredoxin, methylamine dehydrogenase, plastocyanin, rubredoxin, and thioredoxin.

In a further aspect, the insertion sequence or acceptor sequence comprises the catalytic and/or substrate binding site of an enzyme. Suitable enzymes from which such sites are selected include: β-lactamase; acetylcholinesterase; an amylase; barnase; deaminase; a kinase (e.g., such as a tyrosine kinase or serine kinase); a phosphatase; an endonuclease; an exonuclease; an esterase; an enzyme involved in a metabolic pathway (e.g., fructose-1,6-bisphosphatase); a glycosidase; a heat shock protein; a lipase; a lysozyme; a neuramidase/sialidase; a phospholipase; a phosphorylase; a pyrophosphatase; a ribonuclease; a thiolase; a polymerase; an isomerase (such as a mutase; triosephosphate isomerase, xylose isomerase, topoisomerase, gyrase); a lyase (such as aconitase, carbonic anhydrase, pyruvate decarboxylase); an oxidoreductase (such as alcohol dehydrogenase, aldose reductase, a catalase, cytochrome C peroxidase, cytochrome p450, a dehydrogenase, dihydrofolate reductase, glyceraldehydes-3-phosphate dehydrogenase, a hydroxybenzoate hydroxylase, a lactate dehydrogenase, a peroxidase, and a superoxide dismutase); a protease (such as actinidin, α-lytic protease, aminopeptidase, carboxypeptidase, chymosin, chymotrypsin, elastase, endopeptidase, endothiapepsin, HIV protease, Hannuka factor, papain, pepsin, rennin, substilisin, thermolysin, thermitase, and trypsin), a transferase (such as acetyltransferase, aminotransferase, carbamoyltransferase, dihyrolipoamide acetyltransferase, dihydrolipoyl transacetylase, Dihydrolipoamide Succinyltransferase, a nucleotidyl transferase, DNA methyltransferase, formyltransferase, glycosyltransferase, a phosphotransferase, a phosphoribosyltransferase), a dehalogenase, a racemase, and the like.

The catalytic domain also can be a rhodanese homology domain such as forms the active site in various phosphatases and transferases (e.g., such as found in the Cdc25 family of protein dual specificity phosphatases, the MKP1/PAC1 family of MAP-kinase phosphatases, the Pyp1/Pyp2 family of MAP-kinase phosphatases, and certain ubiquitin hydrolases) (see, e.g., Hofmann, et al., 1998, *J. Mol. Biol.* 282: 195-208).

Still other domains can include toxins such as cardiotoxin, conotoxin, erabutoxin, momorcharin, momordin, and ricin.

Other domains include, but are not limited to, signaling domains such as the FHA domain, found in protein kinases and transcription factors such as fork head, DUN1, RAD53, SPK1, cds1, MEK1, KAPP, NIPP1, Ki-67, fraH, and KIAA0170 (see, e.g., Hofmann and Bucher, 1995, *Trends Biochem. Sci.* 20: 347-349); the death domain, a heterodimerization domain present in proteins involved in apoptotic signal transduction and the NFkβ pathway (such as TNFR1, FAS/APO1, NGFR, MORT1/FADD, TRADD, RIP, ankyrin, MyD88, unc-5, unc-44, DAP-kinase, Rb-binding p84, pelle, NFkB, and tube polypeptides) (see, e.g., Hofmann and Tschopp, 1995, *FEBS Lett.* 371: 321-323); and the G-protein desensitization domain (found in ARK1, GRK, G-protein coupled receptor kinases, egl-10, GAIP, BL34 SST2, flbA, RGP3, RGP4Human G0/G1 switch regulatory protein 8, Human B-cell activation protein BL34, and G-protein coupled receptor kinases) (see, e.g., Hofmann and Bucher, "Conserved Sequence Domains in Cell Cycle Regulatory Proteins", abstract presented at the joint ISREC/AACR meeting "Cancer and the Cell cycle", January 1996 in Lausanne).

In one aspect, either the insertion or the acceptor sequence is a light-emitting polypeptide domain such as one obtained from a Green Fluorescent Protein, or modified, or mutant form thereof (collectively referred to as a "GFP"). The wild-type GFP is 238 amino acids in length (Prasher, et al., 1992, *Gene* 111(2): 229-233; Cody et al., *Biochem.* 32(5):1212-1218 (1993); Ormo, et al, 1996, *Science* 273: 1392-1395; and Yang, et al., 1996, *Nat. Biotech.* 14: 1246-1251). Modified forms are described in WO 98/06737 and U.S. Pat. No. 5,777, 079. GFP deletion mutants also can be made. For example, at the N-terminus, it is known that only the first amino acid of the protein may be deleted without loss of fluorescence, while at the C-terminus, up to 7 residues can be deleted without loss of fluorescence (see, e.g., Phillips, et al., 1997, *Current Opin. Structural Biol.* 7: 821).

The insertion sequence or acceptor sequence additionally can comprise the light-reactive portion of a photoreceptor such as bacteriochlorophyll-A, bacteriorhodopsin, photoactive yellow protein, phycocyanin, and rhodopsin.

Additional domain sequences include ligand-binding domains of ligand-binding proteins. Such proteins include, but not limited to: biotin-binding proteins, lipid-binding proteins, periplasmic binding proteins (e.g. maltose binding protein), lectins, serum albumins, immunoglobulins, T Cell Receptors, inactivated enzymes, pheromone-binding proteins, odorant-binding proteins, immunosuppressant-binding proteins (e.g., immunophilins such as cyclophilins and FK506-binding proteins), phosphate-binding proteins, sulfate-binding proteins, and the like. Additional binding proteins are described in De Wolf and Brett, 2000, *Pharmacological Reviews* 52(2): 207-236.]

The domain sequences of the proteins described above are known in the art and can be obtained from a database such as available at the NIH Molecular Modelling Homepage, accessible at http://cmm.info.nih.gov/modeling/pdb_at_a_glance.html.

The insertion and acceptor sequences can be selected from any of the domain sequences described above and can be of like kind (e.g., both catalytic sites, both binding domains, both light emitting domains) or of different kind (e.g., a catalytic site and a binding site, as shown in FIG. 1C; a binding site and a light emitting domain; etc.). The domain sequences can be the minimal sequences required to confer a state or activity or can comprise additional sequences. Other insertion and acceptor sequences can be derived from known domain sequences or from newly identified sequences. Such sequences are also encompassed within the scope of the instant invention.

Exemplary Fusion Molecules

In one aspect, the insertion sequence or the acceptor sequence localizes the fusion molecule intracellularly. Preferably, intracellular localization is coupled to the binding of the fusion molecule to a bio-effective molecule.

In another aspect, the invention provides a fusion protein comprising an insertion sequence and an acceptor sequence, wherein either the inserted sequence or the acceptor sequence binds to a DNA molecule, and wherein DNA binding activity is coupled to the response of the respective other sequence of the fusion molecule to a signal.

The fusion molecule also can comprise an insertion sequence and acceptor sequence, wherein either the inserted sequence or the acceptor sequence associates with a bio-effective molecule, and disassociates from the bio-effective molecule, when the respective other sequence of the fusion binds to a cellular marker of a pathological condition. Such markers can comprise polypeptides, nucleic acids, glycoproteins, lipids, carbohydrates, small molecules, metabolites, pH, ions and the like. Examples of cellular markers of pathological conditions include, but are not limited to cancer-specific or tumor-specific antigens, pathogen-encoded polypeptides (e.g., viral-, bacterial-, protist-, and parasite-encoded polypeptides) as are known in the art.

In still another aspect, the fusion molecule is capable of switching from a non-toxic state to a toxic state. Either the insertion sequence or acceptor sequence may bind to a cellular marker of a pathology (e.g., such as a tumor antigen). Binding of the marker to the fusion protein switches the fusion protein from a non-toxic state or a less toxic state to a toxic state. Similarly, a marker of a healthy cell could be used as a trigger to switch a fusion molecule from a toxic state to a non-toxic state, or to a less toxic state.

In a further aspect, the fusion molecule comprises a molecular switch for controlling a cellular pathway. The fusion molecule comprises an insertion sequence and an acceptor sequence and the states of the insertion sequence and acceptor sequence are coupled, such that the state of either the insertion sequence or the acceptor sequence modulates the activity or expression of a molecular pathway molecule in a cell. Preferably, modulation of activity or expression occurs when the respective other portion of the fusion molecule responds to a signal, e.g., binds to an exogenous or endogenous binding molecule (e.g., ligands, small molecules, ions, metabolites, and the like), responds to electrical or chemical properties of a cell, or responds to the optical environment in which a cell is found (e.g., responding to the presence or absence of particular wavelength(s) of light).

The invention also provides a sensor molecule comprising an insertion sequence and an acceptor sequence, wherein either the insertion sequence or acceptor sequence binds to a target molecule and wherein the respective other sequence generates a signal in response to binding. Preferably, the acceptor sequence comprises a deletion and/or duplication at the insertion site.

It should be obvious to those of skill in the art that these are only exemplary combinations of insertion and acceptor sequences that can be used.

Additional Sequences

Fusion molecules can comprise domain sequences in addition to insertion and acceptor sequences. Such domains can comprise states which may or may not be coupled with the states of the other portions of the fusion molecule.

Additional sequences also can be included as part of the fusion molecule which do not alter substantially the states of the insertion sequence or acceptor sequence portion of the fusion molecule. For example, affinity tag sequences can be provided to facilitate the purification or isolation of the fusion molecule. Thus, His6 tags can be employed (for use with nickel-based affinity columns), as well as epitope tags (e.g., for detection, immunoprecipitation, or FACs analysis), such as myc, BSP biotinylation target sequences of the bacterial enzyme BirA, flu tags, lacZ, GST, and Strep tags I and II. Nucleic acids encoding such tag molecules are commercially available.

Stability sequences can be added to the fusion molecule to protect the molecule from degradation (e.g., by a protease). Suitable stability sequences include, but are not limited to, glycine molecules incorporated after the initiation methionine (e.g., MG or MGG) to protect the fusion molecule from ubiquitination; two pralines incorporated at the C-terminus (conferring protection against carboxypeptidase action), and the like.

In some aspects, the fusion molecule can include a linking or tethering sequence between insertion and acceptor sequences or between insertion or acceptor sequences and other domain sequences. For example, useful linkers include glycine polymers, glycine-serine polymers, glycine-alanine polymers, alanine-serine polymers, alanine polymers, and other flexible linkers as are known in the art (see, e.g., Huston, et al., 1988, *Proc. Natl. Acad. Sci. USA* 85: 4879; U.S. Pat. No. 5,091,513).

These additional sequences can be included to optimize the properties of the fusion molecules described herein.

Generating Fusion Molecules Comprising Domain Insertions

In one aspect, libraries in which an insertion sequence has been randomly inserted into an acceptor sequence are constructed. Preferably, such libraries are generated by randomly inserting a nucleic acid fragment encoding an insertion sequence into a nucleic acid fragment encoding an acceptor sequence.

All existing methods for random insertion can be categorized into one of two strategies: insertion via transposons and insertion after a random double stranded break in DNA using one or a combination of nucleases. A variety of transposons have been used to deliver short, in-frame insertions of 4-93 amino acids (e.g., Hayes and Hallet, 2000, *Trends Microbiol.* 8: 571-7; Manoil and Traxler, 2000, *Methods* 20: 55-61). However, although transposons are an efficient method for delivering an insertion, insertion methods are preferred which create libraries with direct insertions, deletions at the insertion site, or variability in the amount deletions or tandem duplication or variability in the distribution of direct insertions, deletions and tandem duplications.

Random insertion using nuclease treatment, on the other hand, can create such libraries. These methods typically are used for the insertion of short sequences into a target gene during linker scanning mutagenesis. These methods generally differ in the strategy used to produce a random, double-strand break in supercoiled plasmid DNA containing the gene to be inserted.

A number of different strategies can be used to create the fusion molecules of the instant invention. These include, but are not limited to: (a) limited digestion with DNaseI in the presence of $Mn^{2+}$ to produce a single double stranded break (Heffron, et al., 1978, *Proc. Natl. Acad. Sci. USA* 75: 6012-6016); (b) limited digestion with DNaseI in the presence of $Mg^{2+}$ to produce a single nick followed by S1 nuclease treatment to cleave opposite the nick (Dykxhoorn, et al., 1997, *Nucleic Acids Res.* 25: 4209-18); (c) limited digestion with DNaseI with $Mg^{2+}$ under conditions for nick translation to take place, followed by S1 nuclease treatment to cleave opposite the nick; and (d) partial apurination with formic acid and exonuclease III, which introduces a single strand gap at the apurinic site, followed by S1 nuclease treatment to cleave opposite the gap (Luckow, et al., 1987, *Nucleic Acids Res.* 15: 417-429 (1987) summarized in FIG. 2B. In method (b), the location of the double strand break is determined by the location of the DNaseI nicking whereas in method (c) the location of the double strand break is determined by how far nick translation has progressed. In addition to digestion by nucleases (e.g., DNAse, S1, exonucleases, restriction endonucleases and the like), other methods for introducing breaks in sequences can be used. For example, mechanical shearing, chemical treatment, and/or radiation can be used. Generally, the method for introducing breaks is not intended to be limiting.

Figure 2C:
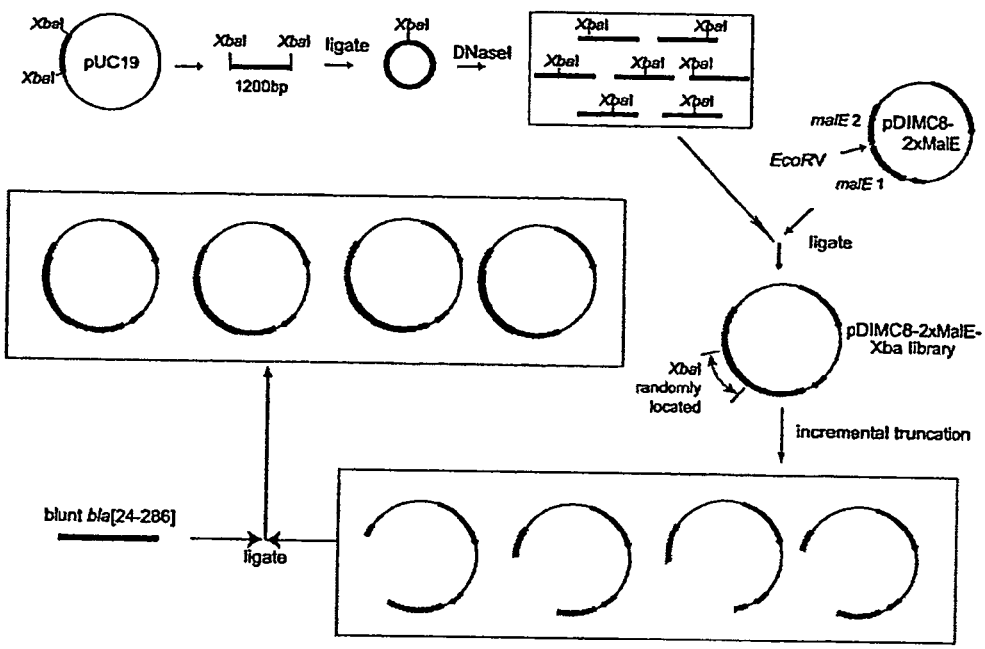

In a particularly preferred aspect, libraries of fusion molecules are generated using incremental truncation (see, patent application Ser. No. 09/718,465 by Ostermeier, "Incrementally Truncated Nucleic Acids and Methods of Making the Same". As shown in FIG. 2C, a key step in the creation of these libraries is the digestion of the gene fragments with a 3' to 5' exonuclease such as Exonuclease III (Exo III) under conditions (e.g., low temperature or in the presence of NaCl) such that the digestion rate is controlled to ~10 bases/minute or less. During Exo III digestion, small aliquots are removed frequently and quenched by addition to a low pH, high salt buffer. Blunt ends are prepared by treatment with a single-strand nuclease and a DNA polymerase followed by unimolecular ligation to recyclize the vector. As Exo III digests DNA at a substantially uniform and synchronous rate (Wu, et al., 1976, *Biochemistry* 15: 734-740), this allows the creation of a library comprising every possible one base pair deletion of a gene or gene fragment.

Constructing a Target Vector Comprising Acceptor Sequences

In one aspect, construction of a library comprises the initial step of constructing and testing a target vector, i.e., a vector comprising a nucleic acid encoding an acceptor sequence. For example, a gene or gene fragment which encodes a polypeptide is cloned into a vector, such as a plasmid. Preferably, the polypeptide exists in a state at least under certain conditions, i.e., comprises an activity, can bind a molecule, exist in a conformation, emit light, transfer electrons, catalyze a substrate, etc. under those conditions.

Preferably, the plasmid comprises a reporter sequence for monitoring the efficacy of the cloning process. Suitable reporter genes include any gene that expresses a detectable gene product which may be RNA or protein. Examples of reporter genes, include, but are not limited to: CAT (chloramphenicol acetyl transferase); luciferase, and other enzyme detection systems, such as β-galactosidase, firefly luciferase, bacterial luciferase, phycobiliproteins (e.g., phycoerythrin); GFP; alkaline phosphatase; and genes encoding proteins conferring drug/antibiotic resistance, or which encode proteins required to complement an auxotrophic phenotype. Other useful reporter genes encode cell surface proteins for which antibodies or ligands are available. Expression of the reporter gene allows cells to be detected or affinity purified by the presence of the surface protein.

The reporter gene also may be a fusion gene that includes a desired transcriptional regulatory sequence, for example, to select for a fusion molecule whose switching functions include the ability to modulate transcription.

Generation of Insertion Sequences

Nucleic acids encoding polypeptide insertion sequences can be obtained via a number of routes, including, but not limited to one or more of: amplification (e.g., using primers which flank a nucleic acid sequence encoding a domain of interest), reverse transcription, cloning, and chemical synthesis.

In one aspect, a nucleic acid can be amplified using primers designed to provide convenient restriction sites or promoter sequences for further cloning steps. This nucleic acid can be cloned into a vector and digested with restriction endonucleases as in FIG. 2A to produce the desired insertion sequence.

Construction of Random Insertion Libraries

In one aspect, a target vector comprising the nucleic acid encoding the acceptor polypeptide is randomly linearized (see, FIGS. 2B and 2C). A variety of different nucleases and digestion schemes can be used. For example, the vector may be exposed to DNase/$Mn^{2+}$ digestion followed by polymerase/ligase repair; S1 nuclease digestion followed by polymerase/ligase repair; and S1 nuclease digestion which is not repaired. The three schemes differ in (a) the methods used to create the random double-stranded break in the target plasmid and (b) whether or not the nucleic acid (e.g., DNA) is repaired by polymerase/ligase treatment, or other methods. However, it should be obvious to those of skill in the art that any method of introducing breaks into a DNA molecule can be used (e.g., such as digestion by mung bean nucleases, endonucleases, restriction enzymes, exposure to chemical agents, irradiation, and/or mechanical shearing) and that the methods of introducing breaks described above are not intended to be limiting.

Preferably, digestion is controlled such that a significant fraction of DNA is undigested in order maximize the amount of linear DNA that only has one double strand break (see, e.g., Example 1, Table 2). Key features for optimizing DNase I digestion include the use of $Mg^{2+}$ free DNaseI (Roche Molecular Biochemicals), a digestion temperature of 22° C. and 1 mM $Mn^{2+}$ instead of $Mg^{2+}$ to increase the ratio of double strand breaks to nicks (see, e.g., as described in Campbell and Jackson, 1980, *J. Biol. Chem* 255: 3726-35).

The DNA can be repaired using methods known in the art, for example, using T4 DNA ligase and T4 DNA polymerase (see, e.g., Graf and Schachman, 1996, *Proc. Natl. Acad. Sci.*

USA 93: 11591-11596) and dephosphorylated. Ligation with nucleic acids encoding the insert is performed and the collection of nucleic acids (e.g., library member).

Incremental truncation libraries can be used to examine all possible insertion points within a given region of an acceptor molecule (see, FIG. 2C). Incremental truncation used within the context of the present invention is a combinatorial solution to identifying active, bisected proteins that would be difficult to predict a priori. Libraries can be recombined in vitro by methods such as DNA shuffling (Stemmer, 1994, Proc. Natl. Acad. Sci. USA 91: 10747-10751) to explore new areas of sequence space (see, e.g., Lutz, et al., 2001, Proc. Natl. Acad. Sci. USA 98: 11248-11253).

Preferably, random insertion libraries according to the invention comprise at least about $10^4$-$10^8$ library members. More preferably, insertion libraries comprise at least two times the number of base pairs in a target nucleic acid (e.g., a nucleic acid comprising acceptor DNA and other vector sequences). More preferably, a library comprises one or more of: deletions at the insertion site and duplications at the insertion site, as well as direct insertions with neither duplications nor deletions. Generally, library members may comprise small deletions or tandem duplications on the order of at least about 1-20 bases; however, larger duplications or deletions on the order of about half the length of a gene also may be tolerated and/or desirable.

Evaluation of Insertion Libraries: Identification of Fusion Molecules

In one aspect, transformants are selected which express a reporter gene included in the target vector, such as a drug resistance gene to initially screen for fusion molecules. Alternatively, or additionally, transformants can be selected in which the state of the insertion sequence is coupled to the state of the acceptor sequence (see, e.g., FIG. 2D). Thus, in one aspect, the existence of each state is assayed for, as is the dependence of each state on existence of one or more other states. States may be assayed for simultaneously, or sequentially, in the same host cell or in clones of host cells. Fusion molecules also can be isolated from host cells (or clones thereof) and their states can be assayed for in vitro.

For example, in one aspect, the enzymatic activity of an insertion sequence or acceptor sequence is assayed for at the same that the binding activity of the respective other portion of the fusion is evaluated (see, e.g., as described further in Example 1, and Table 2) to identify fusion molecules in which enzymatic activity is dependent on binding activity.

In another aspect, fusion molecules are screened for which bind to a molecule, such as a bio-effective molecule (e.g., a drug, therapeutic agent, toxic agent, agent for affecting cellular physiology). The bound fusion molecule is exposed to a cell, and the ability of the fusion molecule to be localized intracellularly is determined. Preferably, release of the bio-effective molecule in response to intracellular localization also is determined.

For example, a cell can be transiently permeabilized (e.g., by exposure to a chemical agent such as $Ca^{2+}$ or by electroporation) and exposed to a fusion molecule associated with the bio-effective molecule (e.g., bound to the bio-effective molecule), allowing the fusion molecule and bound molecule to gain entry into the cell. The ability of the fusion molecule to localize to an intracellular compartment (e.g., to the endoplasmic reticulum, to a lysosomal compartment, nucleus, etc.) along with the bio-effective molecule can be monitored through the presence of a label (e.g., such as a fluorescent label or radioactive label) on the fusion molecule, bio-effective molecule, or both. The label can be conjugated to the fusion molecule and/or the bio-effective molecule using routine chemical methods known in the art. A label also may be provided as part of an additional domain of the fusion molecule. For example, the fusion molecule can comprise a GFP polypeptide or modified form thereof. The localization of the label (and hence the fusion molecule and/or bio-effective molecule) can be determined using light microscopy. Release of the bio-effective molecule can be monitored by lysing the cell, immunoprecipitating the fusion molecule, and detecting the amount of labeled bio-effective molecule in the precipitated fraction.

In one aspect, the cell need not be permeabilized to allow entry of the fusion molecule because the fusion molecule comprises signal sequence that enables the fusion molecule to traverse the cell membrane. Intracellular transport of the bio-effective molecule can be monitored by labeling the bio-effective molecule and examining its localization using light microscopy, FACs analysis, or other methods routine in the art.

In another aspect, insertion libraries are screened for fusion molecules which comprise an insertion sequence or acceptor sequence which associates with a bio-effective molecule and which releases the bio-effective molecule when the respective other portion of the fusion binds to a cellular marker of a pathological condition. Thus, in one aspect, fusion molecules associated with a bio-effective molecule are contacted with cells expressing such a marker and the ability of the fusion molecules to specifically bind to the cell is assayed for, as well as the ability of the fusion molecule to release the bio-effective molecule in response to such binding. For example, as above, either, or both, the fusion molecule and the bio-effective molecule can be labeled and the localization of the molecules determined. The action of the bio-effective molecule also can be monitored (e.g., the effect of the bio-effective molecule on the cell can be monitored).

In a preferred aspect, the insertion library comprises members in which the insertion or acceptor sequence comprises the human serum transferrin (HST) transport domain while the respective other portion of the fusion comprises a binding domain for binding to an anti-cancer drug. In one preferred aspect, the binding domain comprises the methotrexate-binding domain of the dihydrofolate reductase polypeptide (DHFR). At least two methods for the identification of fusions with the desired activity can be used. In the first, a DHFR-HST library is displayed on the surface of phage and panned against methotrexate immobilized on a solid phase such as agarose. Fusions are selected for which bind the drug in the presence of iron at physiological pH (7.4), but which release methotrexate when HST releases its iron in a mildly acidic wash. After each round of selection, the library will be sampled and DHFR activity at physiological and acidic pH will be measured in order to evaluate fusion molecules selected.

The second strategy takes advantage of selective inhibition of bacterial DHFR by the antibacterial drug trimethoprim. E. coli cannot grow in the presence of trimethoprim unless the bacteria is expressing a functional mammalian DHFR. Therefore, in a first step, a non-phage display library of DHFR-HST fusions is expressed in E. coli and those fusions that exhibit DHFR activity is selected by growth on plates at physiological pH containing trimethoprim. Assuming that DHFR activity correlates with methotrexate binding and that conformational changes in the DHFR-HST fusion that disrupt trimethoprim binding also disrupt methotrexate binding, those colonies selected in the first step are screened for no growth on plates at acidic pH containing trimethoprim in order to identify fusions with the ability to release methotrexate at acidic pH.

In still another aspect, insertion libraries are screened for fusion molecules which can switch from a non-toxic state to a toxic state upon binding of the insertion sequence or acceptor sequence to a cellular marker of a pathology. As above, fusion molecules can be selected which specifically bind to cells expressing the marker and the affect of the fusion molecules on cell death can be assayed for. Cell death can be monitored using methods routine in the art, including, but not limited to: staining cells with vital dyes, detecting spectral properties characteristic of dead or dying cells, evaluating the morphology of the cells, examining DNA fragmentation, detecting the presence of proteins associated with cell death, and the like. Cell death also can be evaluated by determining the $LD_{50}$ or $LC_{50}$ of the fusion molecule.

In a further aspect, the insertion library is screened for fusion molecules which comprises a molecular switch for controlling a cellular pathway. Preferably, the states of the insertion sequence and acceptor sequence in the fusion molecules are coupled and responsive to a signal such that in the presence of the signal, the state of either the insertion sequence or the acceptor sequence modulates the activity or expression of a molecular pathway molecule in a cell. A signal can be the presence, absence, or level, of an exogenous or endogenous binding molecule to which either the insertion sequence or acceptor sequence binds, or can be a condition (e.g., chemical, optical, electrical, etc.) in an environment to which the fusion molecule is exposed. The ability of the fusion molecule to control a pathway can be monitored by examining the expression and/or activity of pathway molecules which act downstream of a pathway molecule whose expression and/or activity is being modulated.

In another aspect, fusion molecules are selected in which either the insertion sequence or acceptor sequence binds to a nucleic acid molecule. For example, the ability of fusion molecules to bind to a nucleic acid immobilized on a solid phase can be monitored (e.g., membrane, chip, wafer, particle, slide, column, microbead, microsphere, capillary, and the like). Preferably, fusion molecules are selected in which nucleic acid binding activity is coupled to a change in state of the respective other sequence of the fusion molecule. For example, nucleic acid binding activity can be coupled to the binding activity of another portion of the fusion molecule, catalysis by the other portion, the light emitting function of the other portion, electron transferring ability of the other portion, ability of the other portion to change conformation, and the like. Preferably, nucleic acid binding activity is coupled to the response of the fusion molecule to a signal.

Nucleic acid binding activity also can be monitored by evaluating the activity of a target nucleic acid sequence to which the fusion molecule binds. For example, in one aspect, the fusion molecule binds to a nucleic acid regulatory sequence which modulates the activity (e.g., transcription, translation, replication, recombination, supercoiling) of another nucleic acid molecule to which the regulatory sequence is operably linked. The nucleic acid regulatory molecule and its regulated sequence can be provided as part of a nucleic acid molecule encoding the fusion molecule or can be provided as part of separate molecule(s). The nucleic acid binding activity can be monitored in vitro or in vivo. The ability of fusion molecules to bind to a nucleic acid can also be determined in vivo using one-hybrid or two-hybrid systems (for example, see, Hu, et al., 2000, *Methods* 20: 80-94.

In certain aspects, fusion molecules are selected which bind to a known regulatory sequence or a sequence naturally found in a cell. In other aspects, a sequence which is not known to be a regulatory sequence in a cell is selected for. Preferably, such a sequence binds to the fusion molecule and modulates the activity of another nucleic acid (in cis or in trans), Thus, the fusion molecule can be used to select for novel nucleic acid regulatory sequences. Preferably, the fusion molecule modulates the regulatory activity of the nucleic acid molecule in response to a signal, as described above.

In still a further aspect, the insertion library is screened for fusion molecules which are sensor molecules. Preferably, fusion molecules are screened for in which either the insertion sequence or acceptor sequence binds to a target molecule and wherein the respective other portion of the fusion molecule generates a signal in response to binding. Signals can include: emission of light, transfer of electrons, catalysis of a substrate, binding to a detectable molecule, and the like. To assay for such fusions, members of the library can be screened in the presence of the target molecule (e.g., in solution, or immobilized on a solid support) for the production of the signal.

Evaluation of Structure: State Relationships in Fusion Molecules

Preferably, random library members having desired states are sequenced to precisely identify the sequence of the fusions at the insertion site. More preferably, all library members having desired states are sequenced. Sequence information can be correlated with the ability of different portions of the fusion molecule to maintain one or more states and to respond to one or more signals. A plurality of active insertion points, and preferably, all possible insertion points, can be mapped onto a crystal structure of the acceptor sequence (e.g., such as an acceptor polypeptide). Sites of insertion that produce allosteric control can be compared to sites in the acceptor molecule predicted to be allosterically linked to a signaling molecule (e.g., such as a binding molecule or ligand) by comparisons of the structures of acceptor molecule in the presence or absence of the signaling molecule (see, e.g., Starzyk, et al., 1989, *Biochemistry* 28: 8479-8484).

In another aspect, non-functional fusion molecules also are sequenced to determine structures which are not appropriate to maintain particular states and/or respond to signals.

In a further aspect, fusion molecules are mutagenized to identify molecular switches with optimal properties. Preferably, the sequence of such molecules also are determined. In one aspect, "first round switches" are identified by screening a library of domain insertions and optimized to select for "second round switches" with improved properties. For example, combinatorial (e.g., error-prone PCR, DNA shuffling, etc) and/or rational methods can be used to select for switches with increased activity, stability, and/or improved switching capacity (e.g., ability to respond to a wider or narrow range of signal). Preferably, second round switches are also sequenced to identify sequence alterations associated with improved properties.

Conditional Heterodimerization

Many proteins can have their peptide backbone cut by proteolytic or genetic means, yet the two fragments can associate to make an active heterodimer. This phenomenon of "monomer to heterodimer conversion" is referred to as protein fragment complementation. However, there are many locations where such a conversion it is not feasible, presumably due to inefficient assembly or improper folding of the fragments. This can be overcome by fusion of the fragments to dimerization domains to facilitate correct assembly. Such "assisted protein reassembly" has been shown for a few proteins (Pelletier, et al., 1998, *Proc. Natl. Acad. Sci. USA* 95: 12141-12146; Spencer, et al., 1993, *Science* 262: 1019-24; Michnick, et al., 2000, *Methods Enzymol* 328: 208-30; Remy and Michnick, 1999, *Proc. Natl. Acad. Sci. USA* 96: 5394-

5399, 7620; Remy, et al., 1999, *Science* 283: 990-993; Ghosh, et al., 2000, *J. Am. Chem. Soc.* 122: 5658; Johnson and Varshavsky, 1994, *Proc. Natl. Acad. Sci. USA* 91, 10340-10344; Karimova, et al., 1997, *Proc. Natl. Acad. Sci. USA* 94: 8405-8410; Rossi, et al., 2000, *Methods Enzymol.* 328: 231-51). However, thus far, such methods have been used exclusively in two-hybrid system to evaluate protein-protein interactions (Remy and Micknick, 1999, supra; Arndt, et al., 2000, *J. Mol. Biol.* 295: 627-39; Pelletier, et al., 1999, *Nat Biotechnol* 17: 683-90; Mossner, et al., 2001, *J. Mol Biol* 308: 115-22) and have not been exploited to generate molecular switches.

The invention provides a pair of fusion molecules comprising a first portion and second portion. The first and second portions represent the fragments of a bisected polypeptide which cannot function or exist in a particular state unless both portions are rought into sufficient proximity. Preferably, each portion is fused to an oligomerization omain (see, e.g., FIG. 1B, FIGS. 5A-C, and Example 2 below) thereby generating a pair of fusion molecules. Unlike the protein fragment complementation systems described in the prior art, the fusion molecules according to the invention oligomerize only in the presence of a signal, providing a means to switch ON the activity/state of the polypeptide in the presence of the signal. Suitable signals include any described above for domain insertion fusion molecules.

Suitable oligomerization motifs include, but are not limited to, dimerization motifs such as the LexA dimerization domain (Golemis and Brent, 1992, *Mol. Cell Biol.* 12: 3006), lambda cI dimerization domain, leucine zipper dimerization domains (e.g., such as from GCN4 leucine zippers, antiparallel leucine zippers, p21, and the like), ras GTPase/ras-binding domain, FADD/FAS dimerization domains, EGF receptor dimerization domains, the FKBP/FRAP dimerization domains, the tetramerization domain of p53, and the tetramerization domain of BCR-ABL. In addition, the art also provides a variety of techniques for identifying other naturally occurring oligomerization domains, as well as oligomerization domains derived from mutant or artificial sequences (see, e.g., Zeng et al., 1997, *Gene* 185: 245).

In a preferred aspect, leucine zippers are used as dimerization domains to assemble fragments of a polypeptide. Each domain of a leucine zipper is relatively simple, comprising an approximately 30 amino acid helix. Further, depending on their sequence, leucine zippers can dimerize in a parallel or antiparallel configuration, thus offering two distinct geometries for re-assembly of an active polypeptide. Both parallel and antiparallel leucine zippers have been shown to assist the reassembly of fragments of proteins. Because much is known about the interactions that stabilize dimerization, zippers of different affinity are readily available. Finally, leucine zippers have been shown to be expressed well in *E. coli*.

In one preferred aspect, oligomerization occurs on binding of the oligomerization domains to a small molecule, such as a CID. A CID is a synthetic ligand having two binding surfaces that facilitate the dimerization of domains fused to target proteins (see, e.g., Spencer, et al., 1993, *Science* 262: 1019-24; Rivera, et al., 1998, *Methods* 14: 421-9). CIDs have been used to facilitate the dimerization of domains fused to target proteins. CIDs also have been used to initiate signaling pathways by dimerizing receptors on the cell surface, to translocate cytosolic proteins to the plasma membrane, to import and export proteins from the nucleus, to induce apoptosis, and to regulate gene transcription (Farrar, et al., 2000, supra; Bishop, et al., 2000, *Annu. Rev. Biophys. Biomol. Struct.* 29: 577-606. However, CIDs reported in the art have not been used as switches to activate previously inactive proteins in cells.

Suitable CIDs for use in the present invention include, but are not limited to: the immunosupressant FK506 (Spencer, et al., 1993, supra); coumermycin (which induces dimerization of GyrB-containing fusion proteins) (see, Farrar, et al., 2000, *Methods Enzymol* 327: 421-9), and rapamycin. Novel CID's can be screened for using combinatorial libraries to identify molecules capable of inducing oligomerization of oligomerizing domains.

Types of proteins which can be bisected generally can include any of the domains described above as suitable for insertion sequences or acceptor sequences. In one aspect, bisected molecules include, but are not limited to: dihydrofolate reductase (DHFR) (Pelletier, et al., 1998, *Proc. Natl. Acad. Sci. USA* 95: 12141-12146; Remy, et al., 1999, *Proc. Natl. Acad. Sci. USA* 96: 5394-5399; Remy, et al., 1009, *Science* 283: 990-993); *E. coli* glycinamide ribonucleotide transformylase (PurN) (Michnick, et al., 2000, supra); green fluorescent protein (Ghosh, et al., 2000, *J. Am. Chem. Soc.* 122: 5658), ubiquitin (Johnson and Varshavsky, 1994, *Proc. Natl. Acad. Sci. USA* 91: 10340-10344; Karimova, et al., 1998, *Proc. Natl. Acad. Sci. USA* 95: 5752-6), β-galactosidase (Rossi, et al., 1997, *Proc. Natl. Acad. Sci. USA* 94: 8405-8410; Rossi, et al., 2000, *Methods Enzymol.* 328: 231-51); aminoglycoside and hygromycin B phosphotransferases (Michnick, et al., 2000, supra), as these have been shown to be tolerant of bisections.

Fusion molecules additionally may comprise flexible linkers, stabilizing sequences, affinity sequences, and the like, as described above.

Figure 7A:
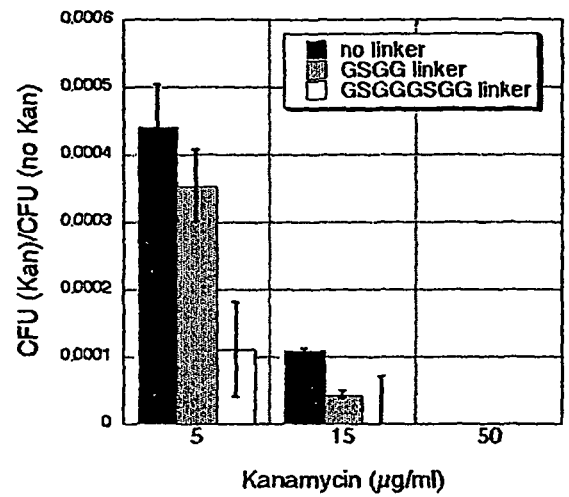
FIG. 7A shows the frequency of active heterodimers of Neo identified from a library of fusion molecules whose assembly is assisted by antiparallel leucine zippers.
Figure 7B:
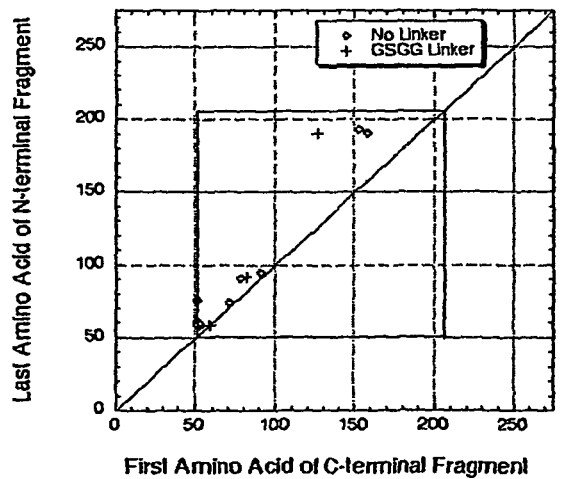
FIG. 7B is a graph summarizing sequence data obtained from libraries comprising heterodimers as in FIG. 7A. Sequences falling on the diagonal line in the graph have no overlap or deletion between fragments. Sequences of heterodimers above the line have overlapping sequences, while those below the line have deleted amino acids. In a library without a flexible linker, sequencing of sixteen randomly selected colonies from kanamycin plates resulted in the identification of ten different heterodimers of Neo (indicated by the large cross) whose assembly is assisted by antiparallel leucine zippers. In a library with a GSGG flexible linker, sequencing of six randomly selected colonies from kanamycin plates resulted in the identification of four different heterodimers of Neo (indicated by the thin-line cross).

In contrast to reassembled proteins described in the art, the conditional heterodimers of the invention may include duplicated residues and/or deletions at the site of bisection. As shown in FIG. 7B, in one aspect, libraries comprising the heterodimers may have small to large duplications and/or deletions in both nucleic acid fragments encoding the respective portions of the bisected polypeptide, increasing the diversity of molecules which may be evaluated for switching function. Further, unlike reassembled proteins described in the art, linker sequences are not required between the dimerization domain and the bisected portion of the polypeptide. Therefore, in one aspect, the invention provides a fusion molecule comprising a portion of a bisected polypeptide fused to an oligomerization domain, wherein the fusion molecule does not comprise a linker sequence and the oligomerization domain is responsive to a signal. Preferably, the response of the oligomerization domain to the signal brings respective portions of the bisected polypeptide together.

In another aspect, the invention provides a pair of fusion molecules which each comprise respective portions of a bisected polypeptide fused to oligomerization domains, wherein the respective portions of the bisected polypeptide are encoded by nucleic acids comprising a duplication or deletion at the bisection site.

Generation of Conditional Heterodimers

Figures 6A, 6B:
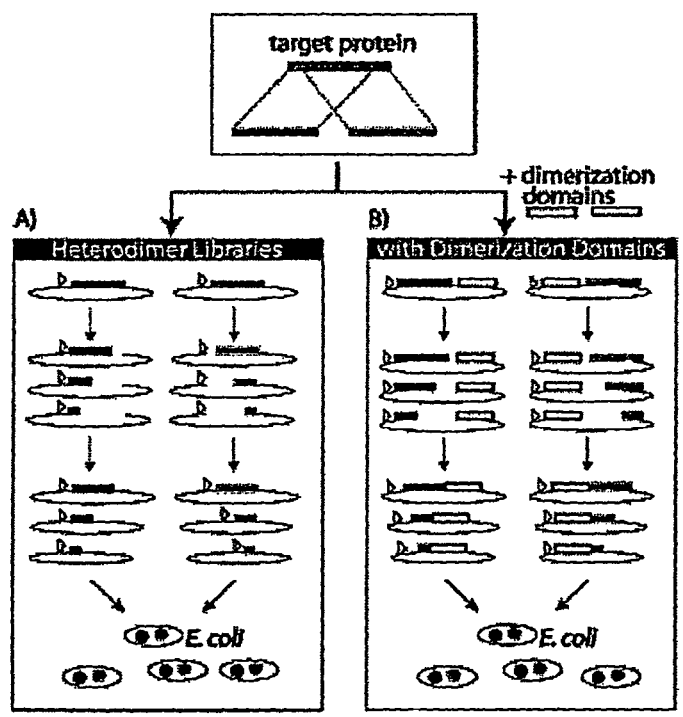
FIGS. 6A-B show strategies to generate libraries of fusion molecules comprising bisected polypeptides fused to oligomerization domains.

The strategy for generating pairs of fusion molecules for forming conditional heterodimers is illustrated in FIGS. 6A-B. In the example shown in the Figures, a polypeptide comprising an activity (e.g., such as an enzymatic activity) is systematically bisected by fragmenting a gene encoding the polypeptide to generate a plurality of bisected polypeptides. Preferably, all possible bisections are represented. In subsequent, or the same cloning steps, nucleic acids encoding oligomerization sequences are ligated in frame to the nucleic acids encoding the plurality of bisected polypeptides. Pairs of fusion molecules so generated are screened for those which are able to dimerize (e.g., restoring the activity of the bisected polypeptides).

In one aspect, incremental truncation is used to engineer a conditional heterodimer. In the example for implementing this approach, shown in FIGS. 6A-B, two overlapping fragments of a gene encoding a polypeptide whose state is to be switched are cloned into vectors. Incremental truncation libraries from the 3' end of the 5' fragment and the 5' end of the 3' fragment are prepared using time-dependent exonuclease digestion (Ostermeier, et al., 1999, *Proc. Natl. Acad. Sci. USA* 96: 3562-3567) or α-phosphothioate nucleotide incorporation (Lutz, et al., 2001, *Nucleic Acids Res.* 29: e16) to generate linear fragments. Preferably, as with domain insertion libraries, these libraries comprise deletions and/or duplications at the insertion site.

To avoid the possibility that individual fragments are active on their own, the starting fragments preferably are designed such that they lack essential residues for functionality (e.g., such as residues at the N-terminal encoding portion or C-terminal encoding portion of the fragments). After truncation, vectors are recircularized such that the 3' truncated fragment is fused to stop-codons in all three reading frames and the 5' truncation is fused to an ATG start codon. Separate libraries of 5' and 3' digested fragments are introduced into *E. coli* at concentrations that will maximize co-transformation of the 5' and 3' fragments, i.e., providing the potential to detect pairs of fusion molecules which dimerize in response to a signal. Nucleic acids encoding oligomerization domains (e.g., such as dimerization domains) can be linked to the fragments before or after or during the creation of the truncation libraries (e.g., by oligo assembly or by PCR). Preferably, the oligomerization domains are responsive to a signal. The ability of cells to recover polypeptide activity in the presence or absence of the oligomerization domain, and in the presence or absence of signal, is monitored.

Cells exhibiting protein activity in the presence of signal are identified and the vectors expressing the respective halves of the polypeptide are sequenced. In one aspect, pairs of fusion molecules exhibiting the highest degree of activity are selected as targets for directed evolution. For example, gene fragments can be amplified by error-prone PCR (Caldwell and Joyce, 1995, in *PCR Primer: A Laboratory Manual*, Cold Spring Harbor Laboratory Press, Plainview, N.Y.) such that on average each DNA molecule has one missense mutation. Such 5' and 3' gene fragments are again co-transformed and cells are selected which express the same or higher levels of activity. Preferably, cells that express higher levels of activity are identified (e.g., at least about 2-fold higher activity). Rescued constructs are sequenced to identify the nature of the mutation and to verify that mutations are not creating fragments whose encoded polypeptides oligomerize even in the absence of an oligomerization domain.

In one aspect, after identifying pairs of fusion molecules whose activity can be restored through oligomerization, the oligomerization domains of these pairs are exchanged for oligomerization domains which are responsive to a signal (e.g., where original domains where not responsive to a signal) or which respond to a different signal from one recognized by domains used to create the original fusion molecules.

Expression Vectors For Expressing Fusion Molecules

Identification of desired fusion molecules, whether domain insertions, or conditional heterodimers, can be facilitated by the use of expression vectors in creating the libraries described above. Such expression vectors additionally can be useful for generating large amounts of fusion molecules (e.g., for delivery to a cell, or organism, for use in vitro or in vivo).

Thus, in one aspect, library members comprise regulatory sequences (e.g., such as promoter sequences) which can be either constitutively active or inducible which are operatively linked to acceptor sequences comprising insertion sequences. Regulatory sequences can comprise promoters and/or enhancer regions from a single gene or can combine regulatory elements of more than one gene. In a preferred embodiment, the regulatory sequences comprise strong promoters which allow high expression in cells, particularly in mammalian cells. For example, the promoter can comprise a CMV promoter and/or a Tet regulatory element.

Library members also can comprise promoters to facilitate in vitro translation (e.g., T7, T4, or SP6 promoters). Such constructs can be used to produce amounts of fusion molecules in sufficient quantity to verify initial screening results (e.g., the ability of the molecules to function as molecular switches).

The expression vectors can be self-replicating extrachromosomal vectors and/or vectors which integrate into a host genome. In one aspect, the expression vectors are designed to have at least two replication systems, allowing them to be replicated and/or expressed and/or integrated in more than one host cell (e.g., a prokaryotic, yeast, insect, and/or mammalian cells). For example, the expression vectors can be replicated and maintained in a prokaryotic cell and then transferred (e.g., by transfection, transformation, electroporation, microinjection, cell fusion, and the like) to a mammalian cell.

The expression vectors can include sequences which facilitate integration into a host genome (e.g., such as a mammalian cell). For example, the expression vector can comprise two homologous sequences flanking the nucleic acid sequence encoding the fusion molecule, facilitating insertion of the nucleic acid expressing the fusion molecule into the host genome through recombination between the flanking sequences and sequences in the host genome. Sequences such as lox-cre sites also can be provided for tissue-specific inversion of the fusion molecule nucleic acid with respect to a regulatory sequence to which the fusion molecule nucleic acid is operably linked.

Integration into the host genome may be monitored by screening for the expression of a reporter sequence included in the expression vector, by the expression of the unique fusion molecule (e.g., by monitoring transcription via Northern Blot analysis or translation by an immunoassay), and/or by the presence of the switching activity in the cell.

Host Cells For Expressing Fusion Molecules

Fusion molecules according to the invention can be expressed in a variety of host cell, including, but not limited to: prokaryotic cells (e.g., *E. coli, Staphylococcus* sp., *Bacillus* sp.); yeast cells (e.g., *Saccharomyces* sp.); insect cells; nematode cells; plant cells; amphibian cells (e.g., *Xenopus*); fish cells (e.g., zebrafish cells); avian cells; and mammalian cells (e.g., human cells, mouse cells, mammalian cell lines, primary cultured mammalian cells, such as from dissected tissues).

The molecules can be expressed in host cells isolated from an organism, host cells which are part of an organism, or host cells which are introduced into an organism. In one aspect, fusion molecules are expressed in host cells in vitro, e.g., in culture. In another aspect, fusion molecules are expressed in a transgenic organism (e.g., a transgenic mouse, rat, rabbit, pig, primate, etc.) that comprises somatic and/or germline cells comprising nucleic acids encoding the fusion molecules.

Fusion molecule also can be introduced into cells in vitro, and the cells (e.g., such as stem cells, hematopoietic cells, lymphocytes, and the like) can be introduced into the host organism. The cells may be heterologous or autologous with respect to the host organism. For example, cells can be obtained from the host organism, fusion molecules introduced into the cells in vitro, and then reintroduced into the host organism.

Methods of Using Molecular Switches In one aspect, the invention provides a method for using a molecular switch to modulate a cellular activity. The cellular activity can include an enzyme activity, the activity of one or more cellular pathway molecules, the transduction of a signal, and the like. Modulation may direct, e.g., the switch itself may alter the activity, or indirect, e.g., the switch may function by delivering a bio-effective molecule to the cell which itself modulates the activity. Modulation can occur in vitro (e.g., in cell culture or in a cell extract) or in vivo (e.g., such as in a transgenic organism). Molecular switches comprising fusion polypeptides also can be administered to a cell by delivering such molecules systemically (e.g., through intravenous, intramuscular, or intraperitoneal injections, or through oral administration of either the polypeptides themselves or nucleic acids encoding the polypeptides) or locally (e.g., via injection into a tumor or into an open surgical field, or through a catheter or other medical access device, or via topical administration).

In one aspect, molecular switches are used to conditionally modulate an enzymatic activity in a cell. For example, a switch molecule can be introduced into a cell that comprises an insertion sequence or acceptor sequence which provides the enzymatic activity. Catalysis by the insertion or acceptor sequence is coupled to the response of the respective other portion of the fusion molecule to a signal, such as binding of the other portion to a molecule (e.g., such as an agent administered to the cell or a naturally occurring small molecule), exposure of the cell to particular chemical conditions (e.g., such as pH), electrical conditions (e.g., potential differences), optical conditions (e.g., exposure of the cell to light of specific wavelengths), magnetic conditions and the like.

In another aspect, a molecular switch is provided which modulates the activity or expression of a molecular pathway molecule in a cell. FIG. 3B shows an example of a switch molecule comprising a pathway molecule which is conditionally active in the presence of a signal (schematically illustrated as in the Figure). The switch molecule is used to alter a cell signaling pathway, e.g., altering the expression and/or activity of downstream pathway molecules (turning such molecules ON or OFF, or altering the level of expression and/or activity of such molecules). In doing so, the switch molecule can be used to regulate fate of one or more cells. Similarly, the molecular switches according to the invention can be used to control metabolic pathways, e.g., providing a fusion molecule which provides an enzymatic activity coupled to the binding of a small molecule, or response to some other signal (see, as shown in FIG. 3E). Preferably, modulation of the enzyme activity in response to the signal, in turn, modulates the expression and/or activity of molecules downstream in the metabolic pathway.

More preferably, the states of the fusion molecules are coupled to a signal, such as the presence of an exogenous or endogenous binding molecules to which either the insertion sequence or acceptor sequence binds. The ability of the fusion molecule to control a pathway can be monitored by examining the expression and/or activity of pathway molecules which act downstream of a pathway molecule whose expression and/or activity is being modulated/controlled by the fusion molecule. Preferably, control of the pathway is coupled to the presence of the signal, e.g., binding of the fusion molecule to the exogenous or endogenous binding molecule, the presence of particular electrical or chemical properties of a cell, the presence or absence of particular wavelength(s) of light, and the like.

Pathways of interest include the phosphatidylinositol-specific phospholipase pathway, which is normally involved with hydrolysis of phosphatidylinositol-4,5-bisphosphate and which results in production of the secondary messengers inositol-1,4,5-trisphosphate and diacylglycerol. Other pathways include, but are not limited to: a kinase pathway, a pathway involving a G Protein Coupled Receptor, a glucerebrosidase-mediated pathway, a cylin pathway, an anaerobic or aerobic metabolic pathway, a blood clotting pathway, and the like.

In still another aspect, a fusion molecule is provided which delivers a bio-effective molecule (e.g., a drug, therapeutic agent, diagnostic or imaging agent, and the like) to a cell. In one scenario, shown in FIG. 3C, the fusion molecule comprises an insertion or acceptor sequence which binds to the bio-effective molecule, while the respective other portion of the fusion binds to a cellular marker that is a signature of a pathology, e.g., a small molecule, polypeptide, nucleic acid, metabolite, whose expression (presence or level) is associated with the pathology. Preferably, the fusion molecule releases the bio-effective molecule only in the presence of the marker of the pathology.

FIG. 3D shows an alternative method of transporting a bio-effective molecule. In this aspect, the insertion sequence or acceptor sequence comprises a transport sequence for transporting a bio-effective molecule bound to the fusion molecule intracellularly. Preferably, the insertion sequence and acceptor sequence are functionally coupled such that a conformational change in the transport sequence is coupled to intracellular release of the bio-effective agent. Successful delivery can be monitored by measuring the effect of the bio-effective agent (e.g., its ability to mediate a drug action or therapeutic effect, or to image a cell). More preferably, the conformation change occurs upon response of the respective other portion of the fusion to a signal (indicated schematically in the Figure as □), enabling conditional intracellular transport of the bio-effective molecule. When the bio-effective agent is delivered to one or more cells in an organism, the effect of the agent on the physiological responses of the organism can be monitored, e.g., by observing clinical or therapeutic endpoints as is routine in the art. Where the bio-effective molecule is an imaging molecule, the localization of the bio-effective molecule in the organism can be monitored by MRI, X-ray, angioplasty, and the like.

Figure 4:
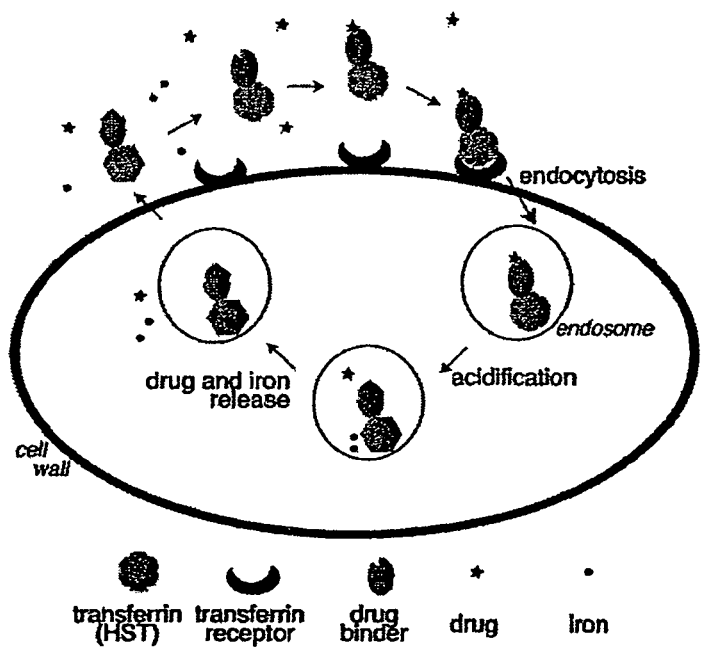
FIG. 4 shows a fusion molecule according to one aspect of the invention which comprises the transferrin domain transport sequence and a methotrexate binding sequence (e.g., such as Dihydrofolate reductase). Outside the cell, the transferrin domain of the 'Trojan horse' fusion protein binds iron and the drug binding domain binds methotrexate. The fusion protein interacts with the transferrin receptor and is endocytosed. A decrease in pH in the endosome causes a conformational change in the transferrin domain resulting in a conformational change in the drug binding domains which occurs concomitant with drug release. The fusion is recycled back outside of the cell to repeat the cycle again.

In one preferred aspect, the transport sequence comprises the human serum tranferrin (HST) polypeptide (see, FIG. 4). HST mediates the transport and uptake of iron into cells. Iron-saturated HST binds to the transferrin receptors on cell surfaces and is internalized by endocytosis. In endosomes, the pH becomes mildly acidic causing the release of iron and a concomitant conformational change in HST. The transferrin-receptor recycles to the surface where HST is released and is free to bind more iron. As tumor cells express high levels of transferrin receptors, several strategies for the targeted delivery of toxic proteins and chemotherapeutic drugs using transferrin uptake pathway have been pursued (Barbas, et al., 1992, *J. Biol. Chem.* 267: 9437-9442; Trowbridge and Domingo, 1981, *Nature* 294: 171-173). A clinical trial has demonstrated that an HST/diphtheria toxin conjugate was effective for the treatment of recurrent malignant brain tumors in humans (see, e.g., Laske, et al., 1997, *Nat. Med.* 3: 1362-1368). HST has been demonstrated to tolerate insertions of peptides while retaining biological activity (see, e.g., Ali et al., 1999, *J. Biol. Chem.* 274: 24066-24073).

Therefore, in one aspect, the insertion sequence or acceptor sequence comprises an HST polypeptide or active portion thereof, while the respective other portion binds to a bioeffective molecule. The binding sequenced-HST sequence functions like a "Trojan horse" for transporting the bio-effective molecule into cells. A suitable binding sequenced can comprise a dihydrofolate reductase (DHFR) which binds to the anti-cancer drug, methotrexate.

As shown in FIG. 4, outside the cell, the transferrin domain of the 'Trojan horse' fusion molecule binds iron and the binding domain binds the drug. The fusion interacts with the transferrin receptor and is endocytosed. A decrease in pH in the endosome causes a conformational change in the transferrin domain, resulting in a conformational change in the drug binding domains which occurs concomitant with drug release. The fusion is recycled back outside of the cell to repeat the cycle again. Because HST has a long circulating half-life and can continuously cycle in and out of the a cell, multiple drug deliveries are possible using this scheme. Delivery of methotrexate can be optimized by selecting for fusion molecules which bind to methotrexate at lower affinities than natural DHFR, e.g., by in silico modeling or from mutagenesis studies (see, e.g., Miller and Benkovic, 1998, *Chem. Biol.* 5: R105-R113).

In still another aspect, the invention provides a method for killing undesired cells, such as abnormally proliferating cells (e.g., cancer cells) (see, e.g., FIG. 3E). For example, a fusion protein comprising a conditionally toxic molecule which targets to a cell having a pathology can be administered a cell (or an organism comprising the cell). Preferably, the toxic state of the fusion protein is coupled to the response of the fusion protein to a signal, such as exposure to a marker of a pathology, causing the fusion protein to switch from a non-toxic state to a toxic state when it encounters the cell comprising the pathology. In one aspect, the change in state from a toxic to a non-toxic or less toxic molecule is coupled to binding of the fusion protein to the marker of the pathology.

In a further aspect, a fusion molecule is provided for regulating an activity of a nucleic acid regulatory sequence in vitro or in vivo. Activities which can be regulated include transcription, translation, replication, recombination, supercoiling, and the like. Preferably, fusion molecules are selected in which binding of the insertion sequence or acceptor sequence of the fusion molecule to the nucleic acid regulatory sequence is coupled to the response of the respective other sequence of the fusion molecule to a signal. Such fusion molecules can be used to create cells with conditional knockouts or knock-ins of a gene product whose expression is mediated by the activity of the nucleic acid regulatory sequence to which the fusion molecule binds, e.g., by providing or withdrawing the signal as appropriate. In one aspect, the signal is a drug or therapeutic agent. In another aspect, the signal is a change in pH, a change in cellular potential, or a change in exposure of a cell (and/or organism) to light. For example, a probe for delivering particular wavelengths of light can be used to provide a highly localized signal to a cell expressing a fusion molecule in vivo.

In still a further aspect, the fusion molecules according to the invention comprise sensor molecules that can be used to detect target analytes in vitro or in vivo (see, FIG. 3G). Target analytes include, but are not limited to: small molecules, metabolites, lipids, glycoproteins, carbohydrates, amino acids, peptides, polypeptides, proteins, antigens, nucleotides, nucleic acids, cells, cell organelles, and small organisms (e.g., microorganisms such as bacteria, yeast, protests, and the like).

The fusion molecule can be exposed to a target molecule in solution or stably associated with a solid support that can be exposed to a sample suspected of containing the target molecule. Alternatively, the fusion molecule can be expressed in a cell, i.e., for detecting intercellular or extracellular targets (for example, where the fusion molecule comprises an extracellular binding domain). Analyte present in the sample will bind to the fusion molecule, triggering production of a signal by the signaling portion of the molecule. Suitable signaling molecules from which this portion can be obtained include molecules capable of emitting light, e.g., such as GFP, or modified, or mutant forms thereof (e.g., EGFP, YFP, CFP, EYFP, ECFP, BFP, and the like). Other signaling molecules include electron transferring domains (e.g., such that the electrical characteristics of the fusion molecule can be monitored to provide a measure of target analyte), binding domains (e.g., domains capable of binding to a labeled molecule), and catalytic domains (e.g., β-lactamase, luciferase, alkaline phosphatase, and the like).

Signaling molecules which comprise catalytic domains can be detected by monitoring changes in the level of a fluorescent substrate. For example, when the catalytic domain is obtained from β-lactamase, fluorescent substrates such as CCF2/FA and CCF2/AM can be used (see, e.g., Zlokarnik, et al., *Science* 279: 84-88 (1998)).

In a further aspect, the invention provides a method for modulating a cellular response by conditionally providing a pair of fusion polypeptides to a cell to mediate the response. For example, the pair of fusion polypeptides can comprise a binding activity, an enzymatic activity, a signaling activity, a metabolic activity, and the like. In one aspect, the pair of fusion polypeptides modulate transcription, translation, or replication of the cell and/or alters a cellular phenotype in response to a signal.

Preferably, each member of the pair comprises a portion of a polypeptide fused to an oligomerization domain. Neither portion by itself can function; however when the portions are brought in proximity to each other, the activity of the polypeptide is restored. In one aspect, oligomerization of the oligomerization domain brings the portions of the polypeptide in proximity to each other and restores the function of the polypeptide. Preferably, oligomerization occurs in response to a signal (e.g., such as the presence of a molecule to which the oligomerization molecules must bind in order to oligomerize).

EXAMPLES

The invention will now be further illustrated with reference to the following examples. It will be appreciated that what follows is by way of example only and that modifications to detail may be made while still falling within the scope of the invention.

Example 1

Generating Fusion Molecules by Domain Insertion

A model system consisting of *E. coli* maltose binding protein ("MBP") as the acceptor polypeptide sequence and the penicillin-hydrolyzing enzyme TEM1 β-lactamase as the insertion polypeptide sequence was chosen to test the combinatorial domain insertion strategy for coupling the two proteins' function. The desired property of the model switch is the ability to modulate β-lactamase activity through changes in maltose concentration (i.e., the switch molecule or fusion protein would behave as an allosteric enzyme).

Construction and Testing of Target Plasmid

The *E. coli* MBP was cloned into plasmid pDIMC8 (Ostermeier and Benkovic, 1999, *Nat. Biotechnol.* 17: 1205-1209) under control of the IPTG inducible tac promoter to create plasmid pDIMC8-Mal. The MIC for ampicillin of DH5α/ pDIMC8-Mal on LB plates was found to be 30-35 µg/ml.

Construction of β-Lactamase Insert DNA

The β-lactamase gene fragment bla [24-286] (encoding for amino acids 24-286 of the β-lactamase gene) was amplified by PCR from pBR322 such that it was flanked by EarI restriction enzymes sites. Attempts to clone this construct into the BamHI site of pACYC184 resulted in very few transformants which, upon characterization, were found to contain plasmids that lacked the β-lactamase gene fragment. Thus, the first DNaseI library (described below) was constructed by digesting the bla[24-286] PCR product with EarI. Subsequently, it was found that the bla[24-286] fragment could be cloned into the pTAdv to create the stable vector pTAdv-plac. Subsequent libraries used a bla[24-286] insert isolated from this plasmid. It is preferable to use a bla[24-286] fragment derived from a plasmid digest since, unlike the PCR product, the insert DNA will be known not to contain any mutations. However, it may be useful in the future to create libraries in which the bla[24-286] insert has been mutated by error-prone PCR (see, Caldwell, 1995, supra). Note that the bla[24-286] fragment for insertion, in this example, does not contain a sequence coding for a flexible linker. However, flexible linkers can be useful for construction of molecular switches.

Construction of Random Insertion Libraries

Plasmid pDIMC8-Mal was randomly linearized using three different methods: (1) DNase/Mn$^{2+}$ digestion followed by polymerase/ligase repair; (2) S1 nuclease digestion followed by polymerase/ligase repair; and (3) S1 nuclease digestion (not repaired). The three protocols differ in (a) the methods used to create the random double-stranded break in the target plasmid and (b) whether or not the DNA was repaired by polymerase/ligase treatment Digestion was controlled such that a significant fraction of DNA was undigested in order maximize the amount of linear DNA that only had one double strand break (see, Table 2). Key features for optimizing the DNase I digestion were the use of Mg$^{2+}$ free DNaseI (Roche Molecular Biochemicals), a digestion temperature of 22° C. and 1 mM Mn$^{2+}$ instead of Mg$^{2+}$ to increase the ratio of double strand breaks to nicks (see, e.g., Campbell and Jackson, 1980, supra).

The DNA was repaired using T4 DNA ligase and T4 DNA polymerase (Graf and Schachman, 1996, *Proc. Natl. Acad. Sci. USA* 93: 11591-11596) (except for method (3)) and dephosphorylated. Ligation with the bla[24-286] insert DNA and transformation into DH5α produced 10$^5$-10$^6$ transformants with a small to large fraction (depending on the method) of the transformants containing the bla[24-286] insert (Table 2).

Preparing the Inserted Gene for Insertion

As an example, the preparation of the DNA of the inserted gene will be described for β-lactamase. All the random insertion methods require that the inserted DNA (bla) be prepared as a linear piece of dsDNA with blunt ends containing only the DNA sequence desired to be inserted. The desired DNA is the DNA that codes for amino acids 24 to 286 of TEM-1 β-lactamase in pBR322 (bla[24-286]). Amino acids 1-23 are not desired because they are the signal sequence that targets β-lactamase to the periplasm. This sequence gets cleaved upon entering the periplasm and is not part of the mature, active β-lactamase. In the fusion constructs, the natural signal sequence of malE will direct the fusions to the periplasm. The bla[24-286] DNA will be prepared as in FIG. 2A by amplifying the DNA such that the sequence is between EarI restriction sites. This DNA is cloned into the BamHI site of pACYC184 to create pACYC-BLA. As shown in FIG. 2A, this construct can be digested with EarI and the bla[24-286] DNA treated with Klenow DNA polymerase to achieve the desired fragment for insertion. This is achieved by virtue of the fact that EarI is a type IIS restriction enzyme that binds a non-palindromic sequence and cleaves outside this sequence.

To achieve the correct geometric configuration and flexibility in the fusions, it may be necessary to include flexible linkers in the fusions at the insertion site. For example, suitable linkers, include, but are not limited to: GlyGlyGlySer on the N-terminus and SerGlyGlyGly on the C-terminus. Linkers can be added by amplifying the bla[24-286] DNA such that the following DNA sequence 5'-GGTGGTGGCAGC-3' is added to the 5' end and the sequence 5'-AGCGGTG- GCGGC-3' is added to the 3' end.

Construction and Characterization of Insertion Libraries

Two general methods are employed: (1) insertion into a plasmid with a random double-stranded break prepared by nuclease digestion and (2) insertion into a gene using CP-ITCHY.

For the former, three related strategies differing in the nature and order of use of the nucleases will be used to construct create a single, double strand break in a plasmid containing the MBP: (1) limited DNaseI digestion in the presence of Mn$^{2+}$, (2) limited DNaseI digestion in the presence of Mg$^{2+}$ to produce a single nick followed by S1 nuclease or mung bean nuclease digestion to cleave opposite the nick (3) limited digestion with S1 nuclease (S1 nuclease can convert supercoiled circular DNA to linear DNA by first making a nick on one of the two strands and then cutting across from this nick (Germond, et al., 1974, *Eur J Biochem* 43: 591-600), particularly under conditions of low ionic strength (Gonikberg, 1979, *Mol. Biol.* (*Mosk*) 13: 1064-9).

Although the first two methods have been used for linker scanning mutagenesis (the random insertion of short sequences), there is little published data on the nature of the sequences at the insertions site of the naïve libraries, and this data is sometimes conflicting. Preferably, for all libraries generated, random members of the naïve libraries are selected and the DNA at the insertion sites sequenced to quantify the distribution and sizes of: deleted DNA, direct insertions and tandemly duplicated DNA at the insertion site. In particular, insertions in which sequences of the insertion sequence are tandemly duplicated may be useful for the same reasons that protein fragments that exhibit protein fragment complementation often have overlapping sequences. Such overlapping sequences are thought to transiently protect exposed regions during folding. Duplications or deletions also are likely to be important for creating molecular switches by affecting the distance and interactions between insertion and acceptor sequences.

Incremental truncation methods also can be used for generating libraries of molecules to provide fusion molecules which have larger deletions and tandem duplications at the insertion site. The size of these tandem duplications (or even deletions) can be controlled by size selection of the library.

Selection of Active Fusions: β-Lactamase-MBP Fusions

Once β-lactamase-MBP insertion libraries have been constructed, they are subjected to selection to identify those library members that have both β-lactamase and MBP activity as well as those in which β-lactamase activity depends on the presence or absence of maltose. The selection scheme is outlined in FIG. 2D. Fusions with a functional β-lactamase domain can be identified by growth of bacteria expressing the fusions on plates containing Amp. Fusions whose β-lactamase activity requires maltose can be identified by plating bacteria on Amp/maltose plates and then replica-plating onto Amp plates to identify clones which grow on the former and do not grow on the latter. Fusions whose β-lactamase activity requires the absence of maltose can be identified by plating bacteria on Amp plates and then replica-plating onto Amp/maltose plates to screen for clones which fail to grow on the former and do grow on the latter.

An alternative screen also is possible. The first screen is carried out as before. On the second screen, the plates will not contain any ampicillin, but still will or will not contain maltose (e.g., the screen is the opposite of the first screen). Filter paper soaked in a nitrocefin solution is overlaid on the colonies for a short period of time. Since nitrocefin is a yellow-colored compound, initially the filter paper will be uniformly yellow (absorbance peak at 390 nm). However, those library members with β-lactamase activity will degrade the nitrocefin to hydrolyzed nitrocefin which is a red compound (absorbance peak at 485 nm) (O'Callaghan, et al., 1972, *Antimicrob. Ag. Chemother.* 1: 283-288). Colonies that fail to turn the filter paper red are identified as those that lack β-lactamase activity under the chosen conditions.

Yet another screen is also possible which relies on the use of Fluorescence Energy Transfer (see, e.g., Zlokarnik, et al., 1998, *Science* 279: 84-88). For example, the substrate CCF2/AM is not charged and can cross the membrane of mammalian cells to enter the cytoplasm where non-specific esterase remove the ester functionalities of the substrate to create CCF2. In CCF2, the cephalosporin core links a 7-hydroxycoumarin to fluorescein. In the intact molecule, excitation of the coumarin results in FRET to the fluorescein, which emits green light. Cleavage of CCF2 by β-lactamase results in spatial separation of the two dyes, disrupting FRET such that excitation of the coumarin now gives rise to blue fluorescence. Charges on CCF2 and its beta-lactamase cleavage products prevent it from leaving the cytoplasm. Thus, FACS and cell sorting can be performed, with and without maltose, to identify fusions in which beta-lactamase activity is dependent on maltose by monitoring FRET. Generally, any substrate comprising a suitable FRET donor and acceptor pair can be used to monitor the enzymatic activity of fusion molecules according to the invention. The above three methods will identify ON/OFF switches (i.e., switches in which maltose has a very large effect on β-lactamase activity). In the event that such ON/OFF switches are sufficiently rare or do not occur, and/or to identify switches in which maltose has a more modest effect, a FRET-based method (e.g., such as based on CCF2) or a spectrophotometric assay can be performed to screen for threshold levels or ranges of β-lactamase activity (see, e.g., Baneyx and Georgiou, 1989, *Enzyme Microb. Technol.* 11: 559-567; Sigal, et al., 1984, *J. Biol. Chem.* 259: 5327-32). Such an assay can be modified for high throughput screening of the activity.

In one aspect, cultures are grown of library members that exhibit β-lactamase activity in the malE⁻ strain PM9F' (Betton and Hofnung, 1994, *EMBO J.* 13: 1226-1234). When grown on minimal plates with maltose as the sole carbon source, cells expressing desired fusions have both β-lactamase activity and the ability to bind maltose. Such cells can be expanded in multi-well plates (e.g., such as microtiter plates), lysed using lysozyme/detergent (e.g., Sambrook, et al., 1989, In *Molecular Cloning: A Laboratory Manual*, Cold Spring Harbor Laboratory, Cold Spring Harbor, N.Y.), and treated with DNase and RNase. The insoluble fraction is removed by centrifugation and the cleared lysates are assayed in the presence and absence of maltose for β-lactamase activity by the measuring a decrease in penicillin G spectrophotometrically at $A_{232}$. Since the goal is to find differences in activity with and without maltose, variations between library members in total fusion protein production, growth of the cells and degree of lysis is not a significant concern.

Evaluation of the Insertion Libraries

Sequencing was performed on random members of the insertion libraries constructed using DNaseI or S1 nuclease (see table below). All sequences were unique and were distributed throughout the plasmid (supporting the randomness of the methods). Both methods created libraries with tandem duplications, direct insertions and deletions. The data strongly suggest that distribution of tandem duplications and deletions in libraries created by the S1 nuclease method were in a much narrower range.

TABLE 1

Location, Orientation And Nature Of Sequences At Insertion Site For DNAse And S1 Nuclease Created Random Domain Insertion Libraries

| Method | % in MalE gene | % in "forward" direction | Deletions (−) Direct insertions (0) Tandem Duplications (+) |
|---|---|---|---|
| DNaseI-repaired library 2 | 75% (15/20) | 40% (8/20) | +18, +7, +1, +1<br>0<br>−5, −13, −16, −17, −42, −48, −54, −56, −75, −162, −191, −263, −340, −379 |
| S1 Nuclease repaired | 45% (5/11) | 27% (3/11) | +5, +4<br>0<br>−1, −1, −2, −2, −5, −6, −22, −101 |

Roughly 1% of the transformants that had a plasmid with a bla[24-286] insert, regardless of the method of library construction, could grow on 50 µg/ml AMP. Randomly selected $Amp^R$ library members were sequenced. All sequences were unique (supporting the 'randomness' of insertion) and Table 2 describes whether they contained deletions, tandem duplications, or neither (direct insertion) and whether both fusion points were in-frame or not. Predominantly the $Amp^R$ colonies had an N-terminal fragment of the MBP gene fused in frame to bla[24-286] with the remaining fragment of the MBP gene being out of frame. The distributions in $Amp^R$ library members suggest that deletions predominate in the DNase I protocol and that not repairing plasmid linearized with S1 nuclease can bias the library toward direct insertions (though the fraction of library members without an insert increases significantly). In DNaseI library #2, 63% (10/16) of library members in the naïve library comprising the β-lactamase gene had it inserted in the MBP gene. This frequency is higher than that expected based solely on the fraction of DNA in the plasmid that codes for the MBP gene since insertions at many locations other than the MBP gene (e.g., $Cm^R$ gene, origin of replication) do not make viable, $Cm^R$ plasmids.

TABLE 2

Comparison of Domain Insertion Libraries

| Method | Distribution Of pDIMC8-Mal After Digestion | Transformants | Frequency Of Transformants With Insert[a] | Frequency of Amp$^R$ Colonies | Deletions (-) Direct Insertions (0) Tandem Duplications (+) In Randomly Selected Amp$^R$ Colonies | Fraction In Frame At Both Crossovers |
|---|---|---|---|---|---|---|
| DnaseI repaired Library #1 | 51% supercoiled 23% nicked 26% linear | ~5 × 10$^5$ | ~0.18 | 0.0017 | -95, -58, -20, -10, -5, -3, -1 0 +1, +51 | 0/10 |
| DnaseI repaired Library #2 | 27% supercoiled 44% nicked 28% linear | ~10 × 10$^5$ | ~0.70 | 0.0079 | -15, -11, -10 -8, -5, 0 +1 | 2/6 |
| S1 nuclease repaired | 24% supercoiled 42% nicked 34% linear | 1.8 × 10$^5$ | ~0.25 | 0.0023 | -2 | 0/1 |
| S1 nuclease (not repaired) | 24% supercoiled 42% nicked 34% linear | 1.0 × 10$^5$ | ~0.06 | 0.0005 | -2 0, 0, 0 | 3/4 |

It is desirable to eliminate members of the library which have β-lactamase activity and consist of an N-terminal fragment of malE fused to an inserted β-lactamase gene with the C-terminal fragment of malE being out of frame with the inserted gene to eliminate members of the library incapable of coupling maltose binding to β-lactamase activity.

Figure 2D:
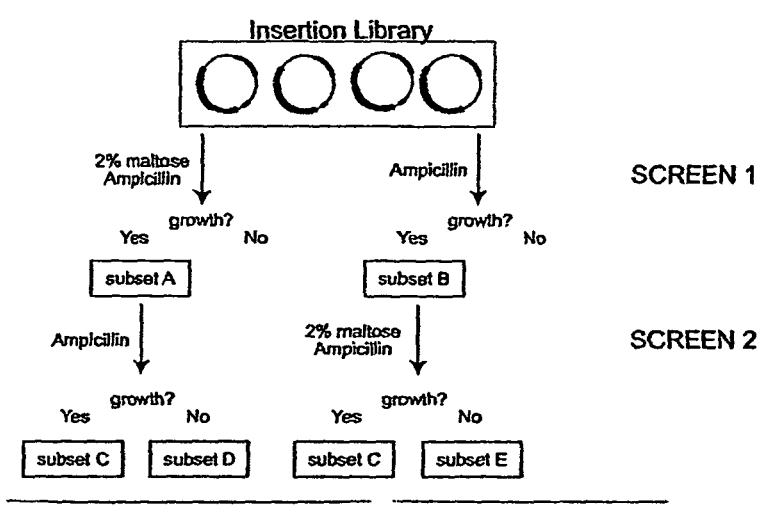

This can be accomplished in a secondary screen by introducing the library into the auxotrophic strain PM9F' which contains a deletion of the MBP gene, growing the bacteria under conditions such that maltose is the sole carbon source and selecting for MBP activity as well as for β-lactamase activity (see, FIG. 2D). Without a functional MBP protein, PM9F' will not grow. In this way, fusions that have a functional insert and can bind maltose will be identified. Table 3 shows three fusions with both beta-lactamase activity and the ability to transport maltose in E. coli identified by this method. As can be seen, the selected fusions consist of both tandem duplications and deletions of the maltose binding protein at the insertion site. One caveat to this secondary screen, however, is that library members that can bind maltose but alter the ability of MBP to interact correctly with other proteins involved in maltose transport (e.g., MalF and MalG) will not be selected.

Table 3 summarizes locations of insertions in fusion molecules which comprise both β-lactamase and MBP activities.

TABLE 3

Locations Of Insertions Found By Random Insertion With Both β-Lactamase And MBP Activities

| Sequence Of Bifunctional Fusions | Net Residues Deleted (-) Or Tandemly Duplicated (+) | Structure Inserted Into | Region Previously Found To Tolerate Short Insertions?* |
|---|---|---|---|
| MBP[1-163]-BLA-MBP[174-397] | -12 | Beta sheet | yes |
| MBP[1-175]-BLA-MBP[179-397] | -5 | Beta sheet | yes |
| MBP[1-246]-BLA-MBP[238-397] | +8 | Beta sheet | No |

*Duplay, et al., 1987,. J Mol Biol 194: 663-73.

An analysis of eighteen randomly selected naïve library members of a DNAse-repaired library, generated as described above, was performed to determine the exact site and orientation of insertions in the library. Thirteen (72%) of the eighteen members of the library included insertion sequences (BLA sequences) inserted at random in the MBP acceptor sequences. The majority of library members (14/18) had deletions of acceptor sequences at the insertion site, though a direct insertion and three tandem duplications were also found. Fifty percent of the library (9/18) had deletions and duplications of less than or equal to eighteen bases. Although large deletions are almost certain to be deleterious for function, small deletions and tandem duplications are an important source of diversity in the library.

From a library of 1.06×10$^6$ transformants of the DNAseI library, 0.8% (approximately 8,000 members) could grow on 50 μg/ml LB/AMP plates indicating a functional β-lactamase protein. Sequencing of plasmid DNA from random Amp$^R$ colonies showed that library members with an N-terminal fragment of the MBP gene fused in frame to bla[24-286] with the remaining fragment of the MBP gene being out of frame predominated this sublibrary. The plasmid DNA from all Amp resistant colonies was isolated en mass and transformed into the MBP auxotroph PM9F', a strain unable to grow on minimal media with maltose as a sole carbon source unless the MBP is provided in trans (Betton and Hofnung, 1994, EMBO J. 13(5): 1226-1234). In the malE auxotroph approximately 10% (i.e., about 800 members) of the sublibrary could grow on a 50 μg/ml AMP minimal plate containing 0.2% maltose, indicating that MBP could transport maltose in E. coli. Analysis of these bifunctional library members indicated that the insertions were predominantly localized to three locations in the MBP protein: near the C-terminus, near residue 170 and near residue 210. Randomly and non-randomly selected library members were sequenced (see, Table 4 below). The sites for successful insertion correlate well with results on linker scanning mutagenesis (random insertion of short DNA sequences) in MBP (see, e.g., Betton, et al., 1993, FEBS Lett. 325 (1-2): 34-8).

TABLE 4

Locations Of Insertions of β-Lactamase into MBP Where Fusions Are Bifunctional*

| Sequence of randomly selected bifunctional BLA-MBP fusions | Sequence of other bifunctional BLA-MBP fusions (not randomly selected) | Sequence of functional MBP variants found by linker scanning mutagenesis** |
|---|---|---|
| T164-166; Δ164-170; T166-175 (2); T167; T167-170 (3); Δ168-184; T172; T179-184 | A163-175; T163 (2); T164; E166/167; T166-167; Δ170-171; Δ175-179 | A134-142 (2)<br>Δ162-177 (3) |
|  | T213-220 | Δ207-216 (3); Δ212-220 (2); E285/286 (3) |
|  | E306/307 | Δ297-312 (3); Δ301 (2); Δ301-306 (3); Δ304-309 (3); Δ304-312 (3) |
| T318 (3)<br>Δ367-368; T369; T362; O367; O370 | Δ367-368; T369-370 |  |

*Δ means deletion of the indicated MBP residues at the insertion point of BLA.
"T" means a tandem duplication of the indicated MBP sequences at the insertion point. The duplicated residues are on either side of the BLA sequence.
"E" means that insertion of BLA was exactly between the indicated residues of MBP.
"O" ("out of frame") is the number of the residue of MBP that the N-terminus of BLA is fused to; the remaining sequence is the out-of-frame sequence that the C-terminus of BLA is fused to.
For the BLA-MBP fusion proteins, the number in parenthesis is the number of times the sequence was found.
For the linker scanning mutagenesis, the number in parenthesis is the number inserted into MBP.
*Betton, et al., 1993, *FEBS Lett*. 325(1-2): 34-8.

Identification of Switches

In an initial examination of the behavior of these bifunctional proteins, overnight inoculums of PM9F9 cells bearing nine of the sequenced members of the library were lysed by French press and the soluble fraction assayed by ntrocefin hydrolysis (O'Callaghan, et al., 1972, *Antimicrob. Ag. Chemother.* 1: 283-288) with and without 50 mM maltose. One member, T369-370 (i.e., comprising a β-lactamase inserted such that amino acids 369 and 370 of MBP were tandemly duplicated on either side), exhibited an increase in velocity in the presence of maltose but not sucrose. Amino acid 370 is the last amino acid of MBP; thus, T369-370 is essentially an end-to-end fusion. Removal of amino acid residues 369 and 370 from the C-terminus to produce an exact end-to-end fusion ("MBP-BLA") resulted in a fusion that exhibited a stimulation of nitrocefin hydrolysis in the presence of maltose of the same magnitude as T369-370. It was unexpected that such an end-to-end fusion would result in a switch since end-to-end fusions of MBP and BLA with linkers have not been reported to behave as switches (see, e.g., Betton, et al., 1997, *Nat. Biotechnology* 15: 1276-1279). In addition, the β-lactamase activity of one of the other nine bifunctional proteins tested that has a similar sequence (□367-368) was not modulated by maltose.

To identify other switches, a semi-rapid throughput assay was developed in which cultures of random bifunctional library members were grown in 96-well format in the presence of IPTG, resulting in the accumulation of the bifunctional protein in the media. The cultures were centrifuged to pellet the cell and the media was assayed spectrophotometrically for the velocity of β-lactamase hydrolysis of nitrocefin in the presence and absence of 5 mM maltose in a 96-well format. The concentration of nictrocefin used was the same as the $K_m$ for nitrocefin of wild-type β-lactamase so that switches in which maltose binding affected either $k_{cat}$ or $K_m$ could be identified. Any culture in which there was a difference in rate of more than 20% (between with and without maltose, to eliminate differences due to variablility in protein production) was selected for further investigation. In a screening of 303 library members, a second library member that showed an increase in velocity of nitrocefin hydrolysis in the presence of maltose, but not in the presence of sucrose or glucose, was found three times—T164-165 (i.e., β-lactamase was inserted such that amino acids 164 and 165 of MBP were tandemly duplicated on either side).

The criteria for bifunctionality in the above screens was quite stringent: the fusions were required to have beta-lactamase activity and to be able to transport maltose in *E. coli*. Transport requires maltose binding, a conformational change in MBP upon maltose binding, and the requisite interactions with membrane proteins MAlG and MalE. Thus, library members that bind maltose but cannot interact with MalG and MalF are not selected (are not bifunctional by definition). The sites for successful insertion of β-lactamase into MBP to make a bifunctional protein correlate quite well with permissive sites in MBP that tolerate short insertions/deletions (Betton, et al., 1993, *FEBS Lett.* 325(1-2): 34-8) and protein bisection (Betton, et al., 1994, *EMBO J.* 13(5): 1226-1234). Thus, the striking observations of those studies—that permissive sites were often within α helical and β strand structural elements—is repeated here. Bifunctional fusion □163-175 deletes an entire β-sheet and bifunctional fusion T213-220 tandemly duplicates two-thirds of an α-helix. Permissive sites for random insertions of GFP into the cAMP-dependent protein kinase regulatory subunit have also included ones within α helices (Biondi, et al., 1998, *Nucleic Acids Res.* 26(21): 4946-4952).

Two of the five permissive sites for linker scanning mutagenesis and protein fragment complementation (~133 and −285) were not observed to be permissive for domain insertion in this study. However, in a previous study, β-lactamase, with 4-5 amino acid linkers on each end, was successfully inserted into MBP at 133 (Betton, et al, 1997, *Nat. Biotechnology* 15: 1276-1279), suggesting that linkers may be required at this site. The reason that insertions at 285 were not found could be that insertions at these locations (a) do not result in folded proteins (b) are not conducive to bβ-lactamase activity or maltose binding or (c) prevent the correct association of MBP with membrane proteins MalG and MalF-an association required for maltose transport. However, with regard to the latter possibility, the sites of interaction between MBP and MalG and MalF (amino acids 13, 14 and 210 which were identified by genetic analysis (Hor and Shuman, 1993, *J. Mol. Biol.* 233(4): 659-70) are distal to amino acid 285.

Kinetic Characterization of Switches

In one aspect, the kinetic constants and binding constants of the original wildtype genes, the two switches (T164-165 and MBP-BLA) and two bifunctional non-switches with similar sequences to the switches (T164 and □367-368) were determined from Eadie-Hofstee plots and Eadie plot equivalents, respectively, using a spectrophotometric assay for nitrocefin hydrolysis (Sigal, et al., 1984, *J. Biol. Chem.* 259 (8): 5327-32). The results of this assay are summarized in Table 5, below.

TABLE 5

Kinetic And Binding Constants Of β-Lactamase-MBP Molecular Switches[a]

| Sequence | $K_d$ maltose (μM) | $K_m$ nitrocefin (μM) | | $k_{cat}$ (+maltose) $k_{cat}$ (−maltose) | $k_{cat}/K_m$ (+maltose) $k_{cat}/K_m$ (−maltose) |
|---|---|---|---|---|---|
| | | 5 mM Maltose | No maltose | | |
| β-lactamase + MBP[b] | 1 – 1.5[c] | 47 ± 6 | 44 ± 3 | 1.0 ± 0.1 | 1.0 ± 0.2 |
| T164-165 | 3.2 ± 1.0 | 45 ± 4 | 61 ± 8 | 1.4 ± 0.1 | 1.9 ± 0.3 |
| T369-370 | ~10 | ~42 | ~34 | ~1.7 | |
| MBP-BLA | 14 ± 7 | 46 ± 3 | 30 ± 3 | 1.8 ± 0.1 | 1.2 ± 0.2 |

[a]Conditions: 22° C., 0.1 M phosphate (pH 7.0) 1 mM EDTA (+5 mM maltose where indicated);
[b]lactamase and MBP present as separate proteins;
[c]Schwartz et. al(Schwartz, Kellermann et al. 1976)

Following such a procedure, the Eadie-Hofstee plots for the fusion proteins were linear indicating that the Michaelis-Menten equation holds for the switches. The dissociation content of the switches for maltose was determined using change in velocity of nitrocefin hydrolysis as a signal. The absolute values of $k_{cat}$ are not known since the total protein concentration is not known. The relative $k_{cat}$'s (and also the relative specificity constants) that compare with and without maltose can be determined because the enzyme concentration, though unknown, is the same for both measurements of $V_{max}$. The measurements of $K_m$ for nitrocefin observed herein closely match that of a previous study (54.7 μM) (see, Raquet, et al., 1994, *J. Mol. Biol.* 244(5): 625-39).

The end-to-end fusion shows a larger increase in $k_{cat}$ than T164-164 did (80% vs. 40%) but this is compensated for by an increase in $K_m$ for the end-to-end fusion. T164-165 shows both an increase in $k_{cat}$ and a decrease in $K_m$ in the presence of maltose and also shows an increase of $k_{cat}/K_m$ (90%) in the presence of maltose. T164-165 was also the most sensitive switch, with a $K_D$ for maltose close to that of the wildtype MBP. All of the above kinetic characterization was performed on the media fraction; however, T164-165, in which a His-tag has been added, was b purified by nickel affinity chromatography to high purity and has been shown to exhibit switching behavior comparable to what was seen in the media fraction.

Switching Behavior Correlates with a Conformational Change in MBP

Although MBP can bind many other linear maltodextrins, cyclodextrins and reduced or oxidized variants thereof, only those ligands which induce a conformational change in MBP (Hall, et al. (1997) *J. Biol. Chem.* 272(28): 17605-17609; Hall, et al. (1997) *J. Biol. Chem.* 272(28): 17610-17614) behaved as a switch (see, FIG. 8). Binding of β-cyclodextrin (which does not produce a conformational change) was confirmed by competition experiments in which maltose's effected on β-lactamase could be competed away with these sugards. This suggests conformational change in MBP upon ligand binding as a mechanism for the coupling achieved between maltose binding and nitrocefin hydrolysis.

The switches apparently function as monomeric enzymes that derive from the covalent linkage of non-interacting, monomeric proteins with the prerequisite binding and catalytic functionalities, respectively.

Example 2

MBP:GFP Fusions

Maltose Binding Protein (MBP) and GFP fusion molecules are generated essentially as described above.

Selection of Active Fusions: GFP-MBP

*E. coli* cells expressing GFP can be sorted based on fluorescence and other parameters using flow cytometry (Daugherty, et al., 2000, *Proc. Natl. Acad. Sci. USA* 97: 2029-34). Initially, *E. coli* cells expressing GFP-MBP fusions library are screened to identify cells with significant green fluorescence and which grown in the presence of maltose (provided in both in the growth medium and during the sorting process) as well to identify cells that have significant green fluorescence without maltose (absent in both the growth medium and during the sorting process). Cells selected are re-cultured and cells are sorted for the absence of, or a decrease in, fluorescence under the opposite condition (e.g., in the absence of maltose where cells were previously grown in the presence of maltose, and in the presence of maltose where cells were previously grown in the absence of maltose). Cells selected in this second sorting process are plated on LB plates with the level of maltose from the first sort to confirm that a lack of fluorescence is not due to reasons other than the effect of maltose (e.g., such as loss of plasmid, deletion of the MBP gene, mutations, etc.).

As in Example 1, secondary screens can be used to eliminate library members in which the insertion sequence and the acceptor sequence are out of frame.

Example 3

Generation of Conditional Heterodimers

As a model system, control over the neomycin resistance protein (Neo) (aminoglycoside phosphotransferase APH(3')-IIa), by conditional heterodimerization is engineered. Incremental truncation libraries of fragments of Neo are used to identify bisection locations in Neo that do not abolish activity by selection on plates that contain kanamycin.

Design of Overlapping Fragments of Neo

To avoid the possibility of individual fragments of Neo being active on their own, the starting fragments for incremental truncation are designed such that they lack essential residues for functionality because they are already N-terminally or C-terminally truncated. The seven classes of APHs have very little general sequence homology (Wright, 1999, *Front Biosci.* 4: D9-21). However, a sequence alignment of representative members of each class, combined with the known functions of residues in APH(3')-IIIa (Wright and Thompson, 1999, *Front Biosci.* 4: D9-21) suggest that C-terminal fragment Neo[51-264] will be inactive since it lacks K50 (equivalent to K44 in APH(3')-Ma) and that N-terminal fragment Neo[1-207] will be inactive since it lacks D208 (equivalent to D208 in APH(3')-IIIa). This is a very conservative selection of fragments as it is likely that fragments longer than the ones chosen will also be inactive on their own.

Incremental truncation libraries of the same overlapping fragments are fused to parallel and antiparallel leucine zippers and are selected on plates containing kanamycin. Preferably, cotransformants are plated on increasing amounts of kanamycin and plated under different conditions (temperature and IPTG level) to select for heterodimers of Neo that confer kanamycin resistance. Plasmid DNA from randomly selected $Kan^R$ colonies are isolated and re-transformed separately, and together, to confirm that the $Kan^R$ phenotype requires both vectors. The plasmid DNA is then sequenced to identify the DNA that codes for complementing fragments.

Neo fragments that are functional only when fused to leucine zippers can thus be identified. Fusion molecules whose assembly occur when fused to leucine zippers (e.g., forming functional Neo polypeptides) can be subjected to directed evolution (Arnold, et al., 2001, *Trends Biochem. Sci.* 26: 100-6) to overcome these shortcomings.

Fragments improved by directed evolution (e.g., pairs of fusion molecules which display at least 2-fold greater activity, preferably, at least 5-fold, and more preferably, at least ten-fold activity) are fused to dimerization domains that require a CID, thereby coupling Neo activity to the presence or absence of the CID will create Neo activity that is dependent on the CID. For example, fragments of Neo can be fused to GyrB and tested to see if kanamycin resistance depends on coumermycin or to FK506-binding protein (FKBP) tested to see if kanamycin resistance depends on rapamycin. Preferably, fragments whose activities are improved are sequenced to identify relationships between types of mutations and increases in activity. In some aspects, fragments whose activities are not improved or which are actually diminished also are sequenced.

Construction of Control Vector

The neo gene is amplified from plasmid pSV2-Neo by overlap extension PCR (to s remove an internal NcoI site that creates problems for doing the C-terminal truncation) and cloned into the NdeI/SpeI sites of pDIM-N2 to create pDIM-N2-Neo(NcoI$^-$).

Construction and Testing of Vectors for Incremental Truncation for Protein Fragment Complementation (No Leucine Zippers)

The DNA coding for fragments Neo[1-207] and Neo [51-264] is amplified by PCR from pDIM-N2-Neo(NcoI$^-$) and cloned into the NdeI/BamHI sites of pDIMN2 and the BglII/SpeI sites of pDIMC8. The MIC of kanamycin on DH5α on LB plates is determined to verify that pDIMN2-Neo[1-207] and pDIMC8-Neo[51-264], either separately, or together, do not increase the MIC (i.e., to confirm that these fragments are not active by themselves).

Determination of the Maximum Rate of Recombination

Recombination between pDIMN2 and pDIMC8 plasmids, even in recA mutants, can reassemble an intact gene (see, e.g., Ostermeier et al., 1999, *Proc. Natl. Acad. Sci. USA* 96: 3562-3567). Thus, in one aspect, the maximum frequency of recombination is determined by co-transforming pDIMN2-Neo[1-207] and pDIMC8-Neo[51-264] and plating a large number of cells on plates containing various amounts of kanamycin to identify clones in which neomycin activity is restored (e.g., clones in which recombination is likely to have occurred). This provides a baseline for determining the amount of background in the library (e.g., the likely number of false positive results obtained).

Construction and Testing of Incremental Truncation Libraries without Leucine Zippers Individual incremental truncation libraries (~1×10$^6$ each) were constructed by a protocol previously described by Ostermeier, et al., 2002, In *Protein-Protein Interactions: A Molecular Cloning Manual*, E. Golemis. Cold Spring Harbor, N.Y., Cold Spring Harbor Laboratory Press. PCR (with primers outside the truncation region) on random colonies confirmed the desired range of truncation. These libraries were co-transformed into DH5α to create a library of 2.5×10$^6$ transformants, an order of magnitude larger than the number of possible combinations (=471$^2$) of truncation lengths of the two libraries. These libraries were then plated at 22° C. and 37° C. on plates with or without IPTG containing 5 or 50 μg/ml kanamycin. The frequency of colonies was not a significant function of growth temperature or IPTG and averaged 0.00022 CFU (5 μg/ml Kan)/CFU (no Kan) and 0.00005 CFU (50 μg/ml Kan)/CFU (no Kan). Twenty-seven colonies were analyzed and found to be 'large-plasmid' recombinants or pDIM-N2-Neo(NcoI$^-$) contamination. Thus, the Neo gene cannot be fragmented between DNA coding for residues 51 and 207 to produce to gene fragments capable of producing enough protein with enough activity to provide kanamycin resistance above background. In other words, Neo is not amenable to unassisted protein reassembly.

Construction of Incremental Truncation Libraries of Neo Fused to Antiparallel Leucine Zippers The individual incremental truncation libraries were constructed such that fragments of Neo were fused on the truncation side to DNA coding for antiparallel leucine zippers based on those designed by Ghosh, et al., 2000, *J. Am. Chem. Soc.* 122: 5658. Three different libraries were constructed, varying in the nature of the flexible linker between the leucine zipper and the truncated gene: (a) no linker, (b) GSGG linker and (c) GSGGGSGG linker. The frequency of $Kan^R$ colonies was not a significant function of IPTG; however, approximately 4-10 fold more colonies grew at 22° C. than at 37° C. suggesting folding/aggregation problems in many of the fragments. The frequency of recombination was found to be stimulated by the presence of the zipper sequences, though the level of recombination was 2-4 lower than the maximum frequency of recombination determined earlier. The frequency of $Kan^R$ colonies that were not recombinants ('true positives'; at 37° C. on plates without IPTG) are shown in FIG. 7A as a function of kanamycin concentration. Libraries with fragments of Neo fused to parallel leucine zippers also resulted in conditional heterodimers with similar sequences, but at a significantly lower frequency.

Randomly selected true positives were selected and the DNA of the fragments sequenced. The plasmid DNA from these true positives was retransformed to confirm that $Kan^R$ only resulted from the presence of both plasmids. Thus, the method demonstrates the successful generation of molecular switches that form an active aminoglycoside phosphotransferase IIa (Neo) protein (capable of hydrolyzing the antibiotic kanamycin) only when fused to antiparallel leucine zippers. Upwards of twenty distinct heterodimers whose bisection loci cluster in three regions (FIG. 7B) have been readily identified through selection on kanamycin plates even though amenable loci pairs occur at a frequency of less than 1 for every 2000 possible bisection loci. These fragments often had significant overlap and some loci were proximal to the active site making it unlikely these loci could have been identified through rational design.

Although conversion to a conditional heterodimer severely compromised the Neo resistance of cells by approximately two orders of magnitude, high level Neo resistance (in one case, up to wildtype levels of ~500 μg/ml) has been restored by one round of random mutagenesis (using error-prone PCR under conditions such that approximately one mutation per fragment results) and selection on 10$^6$ variants of two different conditional heterodimers (Neo[1-59]zip/zipNeo[59-264]

and Neo[1-91]zip/zipNeo[78-264]). For the case of Neo[1-59]zip/zipNeo[59-264] the following sets of mutation were found in a random sampling of the improved variants that could grow at ~500 µg/ml: C31R/K175E/V198E, C31R/M120L, N58S/R177S/V198E, C31R/D52Q/D118E/Q155L. The improvement ostensibly resulted from an increase in the kinetic properties of the conditional heterodimers since the two "evolved", zipperless Neo fragments (Neo fragments with mutations but without leucine zippers) could not provide kanamycin resistance and the expression level of the "unevolved" heterodimers and the "evolved" heterodimers (both with leucine zippers) were very similar as determined by a quantitative ELISA assay using antibodies against Neo.

Variations, modifications, and other implementations of what is described herein will occur to those of ordinary skill in the art without departing from the spirit and scope of the invention and the following claims.

All patents, patent applications, a publications, referenced herein are incorporated in their entirety herein.

What is claimed is:

1. A method for assembling a modulatable fusion polypeptide, comprising:
   a) creating an insertion nucleic acid sequence library comprising the steps of:
      i) obtaining an insertion nucleic acid sequence which encodes a polypeptide that recognizes a signal of interest;
      ii) ligating the insertion nucleic acid sequence under conditions sufficient to circularize the insertion nucleic acid sequence;
      iii) digesting the insertion nucleic acid sequence of ii) under conditions sufficient to randomly introduce a double-stranded break to create the insertion nucleic acid sequence library;
   b) creating an acceptor nucleic acid sequence library comprising the steps of:
      i) obtaining an acceptor nucleic acid sequence which encodes a polypeptide that produces a measurable change in a desired state, provided the measurable change in state is not fluorescence;
      ii) ligating the acceptor nucleic acid sequence under conditions sufficient to circularize an insertion nucleic acid sequence;
      iii) digesting the acceptor nucleic acid sequence of ii) under conditions sufficient to randomly introduce a double-stranded break to create an acceptor nucleic acid sequence library;
   c) ligating the nucleic acids of the libraries of a) and b) under sufficient conditions such that an insertion nucleic acid sequence will randomly insert into the randomly introduced double strand break in an acceptor nucleic acid sequence;
   d) transforming a suitable host with the ligated libraries of c);
   e) selecting for a transformed host expressing the modulatable fusion polypeptide by exposing the transformed host to the signal of interest and identifying the transformed host which exhibits a measurable change of the desired state.

2. The method of claim 1 wherein the modulatable polypeptide can switch between at least an active state and a less active state.

3. The method of claim 1, wherein the creation of a random double strand break into an acceptor nucleic acid sequence is carried out by a method selected from: nuclease treatment, mechanical shearing, chemical treatment or radiation treatment.

4. The method of claim 1, 2, or 3, wherein the method further comprises generating a duplication, deletion, substitution at the insertion site in an acceptor nucleic acid sequence.

5. The method of claim 3, wherein nuclease treatment comprises digestion with a 3' to 5' exonuclease.

6. The method of claim 1, wherein the insertion nucleic acid sequence encodes a polypeptide consisting of β-lactamase, and the acceptor nucleic acid sequence encodes a polypeptide consisting of maltose binding protein.

* * * * *

```
                        SEQUENCE LISTING

<160> NUMBER OF SEQ ID NOS: 41

<210> SEQ ID NO 1
<211> LENGTH: 4
<212> TYPE: PRT
<213> ORGANISM: Artificial Sequence
<220> FEATURE:
<223> OTHER INFORMATION: Description of Artificial Sequence: Synthetic
      linker sequence

<400> SEQUENCE: 1

Gly Ser Gly Gly
  1

<210> SEQ ID NO 2
<211> LENGTH: 37
<212> TYPE: PRT
<213> ORGANISM: Homo sapiens

<400> SEQUENCE: 2

Pro Asn Lys Gly Ser Gly Thr Thr Ser Gly Thr Thr Arg Leu Leu Ser
  1               5                  10                  15

Gly His Thr Cys Phe Thr Leu Thr Gly Leu Leu Gly Thr Leu Val Thr
                 20                  25                  30

Met Gly Leu Leu Thr
         35

<210> SEQ ID NO 3
<211> LENGTH: 14
<212> TYPE: PRT
<213> ORGANISM: Unknown Organism
<220> FEATURE:
<223> OTHER INFORMATION: Description of Unknown Organism: Myristylation
      src amino acid sequence

<400> SEQUENCE: 3

Met Gly Ser Ser Lys Ser Lys Pro Lys Asp Pro Ser Gln Arg
  1               5                  10

<210> SEQ ID NO 4
<211> LENGTH: 25
<212> TYPE: PRT
<213> ORGANISM: Unknown Organism
<220> FEATURE:
<223> OTHER INFORMATION: Description of Unknown Organism: Palmitoylation
      GRK6 amino acid sequence

<400> SEQUENCE: 4

Leu Leu Gln Arg Leu Phe Ser Arg Gln Asp Cys Cys Gly Asn Cys Ser
  1               5                  10                  15

Asp Ser Glu Glu Glu Leu Pro Thr Arg
                 20                  25
```

-continued

```
<210> SEQ ID NO 5
<211> LENGTH: 7
<212> TYPE: PRT
<213> ORGANISM: Monkey virus

<400> SEQUENCE: 5

Pro Lys Lys Lys Lys Lys Val
 1               5

<210> SEQ ID NO 6
<211> LENGTH: 6
<212> TYPE: PRT
<213> ORGANISM: Homo sapiens

<400> SEQUENCE: 6

Ala Arg Arg Arg Arg Pro
 1               5

<210> SEQ ID NO 7
<211> LENGTH: 10
<212> TYPE: PRT
<213> ORGANISM: Unknown Organism
<220> FEATURE:
<223> OTHER INFORMATION: Description of Unknown Organism: NF kB p50
      amino acid sequence

<400> SEQUENCE: 7

Glu Glu Val Gln Arg Lys Arg Gln Lys Leu
 1               5                  10

<210> SEQ ID NO 8
<211> LENGTH: 9
<212> TYPE: PRT
<213> ORGANISM: Unknown Organism
<220> FEATURE:
<223> OTHER INFORMATION: Description of Unknown Organism: NF kB p65
      amino acid sequence

<400> SEQUENCE: 8

Glu Glu Lys Arg Lys Arg Thr Tyr Glu
 1               5

<210> SEQ ID NO 9
<211> LENGTH: 21
<212> TYPE: PRT
<213> ORGANISM: Unknown Organism
<220> FEATURE:
<223> OTHER INFORMATION: Description of Unknown Organism: Nucleoplasmin
      amino acid sequence

<400> SEQUENCE: 9

Ala Val Lys Arg Pro Ala Ala Thr Leu Lys Lys Ala Gly Gln Ala Lys
 1               5                  10                  15

Lys Lys Lys Leu Asp
            20

<210> SEQ ID NO 10
<211> LENGTH: 5
<212> TYPE: PRT
<213> ORGANISM: Homo sapiens

<400> SEQUENCE: 10

Lys Phe Glu Arg Gln
 1               5

<210> SEQ ID NO 11
<211> LENGTH: 36
```

```
<212> TYPE: PRT
<213> ORGANISM: Homo sapiens

<400> SEQUENCE: 11

Met Leu Ile Pro Ile Ala Gly Phe Phe Ala Leu Ala Gly Leu Val Leu
 1               5                  10                  15

Ile Val Leu Ile Ala Tyr Leu Ile Gly Arg Lys Arg Ser His Ala Gly
                20                  25                  30

Tyr Gln Thr Ile
            35

<210> SEQ ID NO 12
<211> LENGTH: 35
<212> TYPE: PRT
<213> ORGANISM: Homo sapiens

<400> SEQUENCE: 12

Leu Val Pro Ile Ala Val Gly Ala Ala Leu Ala Gly Val Leu Ile Leu
 1               5                  10                  15

Val Leu Leu Ala Tyr Phe Ile Gly Leu Lys His His Ala Gly Tyr
                20                  25                  30

Glu Gln Phe
        35

<210> SEQ ID NO 13
<211> LENGTH: 27
<212> TYPE: PRT
<213> ORGANISM: Saccharomyces sp.

<400> SEQUENCE: 13

Met Leu Arg Thr Ser Ser Leu Phe Thr Arg Arg Val Gln Pro Ser Leu
 1               5                  10                  15

Phe Ser Arg Asn Ile Leu Arg Leu Gln Ser Thr
                20                  25

<210> SEQ ID NO 14
<211> LENGTH: 25
<212> TYPE: PRT
<213> ORGANISM: Saccharomyces sp.

<400> SEQUENCE: 14

Met Leu Ser Leu Arg Gln Ser Ile Arg Phe Phe Lys Pro Ala Thr Arg
 1               5                  10                  15

Thr Leu Cys Ser Ser Arg Tyr Leu Leu
                20                  25

<210> SEQ ID NO 15
<211> LENGTH: 64
<212> TYPE: PRT
<213> ORGANISM: Saccharomyces sp.

<400> SEQUENCE: 15

Met Phe Ser Met Leu Ser Lys Arg Trp Ala Gln Arg Thr Leu Ser Lys
 1               5                  10                  15

Ser Phe Tyr Ser Thr Ala Thr Gly Ala Ala Ser Lys Ser Gly Lys Leu
                20                  25                  30

Thr Gln Lys Leu Val Thr Ala Gly Val Ala Ala Ala Gly Ile Thr Ala
            35                  40                  45

Ser Thr Leu Leu Tyr Ala Asp Ser Leu Thr Ala Glu Ala Met Thr Ala
        50                  55                  60
```

-continued

<210> SEQ ID NO 16
<211> LENGTH: 41
<212> TYPE: PRT
<213> ORGANISM: Saccharomyces sp.

<400> SEQUENCE: 16

Met Lys Ser Phe Ile Thr Arg Asn Lys Thr Ala Ile Leu Ala Thr Val
 1               5                  10                  15

Ala Ala Thr Gly Thr Ala Ile Gly Ala Tyr Tyr Tyr Asn Gln Leu
            20                  25                  30

Gln Gln Gln Gln Gln Arg Gly Lys Lys
        35                  40

<210> SEQ ID NO 17
<211> LENGTH: 4
<212> TYPE: PRT
<213> ORGANISM: Unknown Organism
<220> FEATURE:
<223> OTHER INFORMATION: Description of Unknown Organism: Protein
      sequence from calreticulin

<400> SEQUENCE: 17

Lys Asp Glu Leu
 1

<210> SEQ ID NO 18
<211> LENGTH: 15
<212> TYPE: PRT
<213> ORGANISM: Human adenovirus

<400> SEQUENCE: 18

Leu Tyr Leu Ser Arg Arg Ser Phe Ile Asp Glu Lys Lys Met Pro
 1               5                  10                  15

<210> SEQ ID NO 19
<211> LENGTH: 20
<212> TYPE: PRT
<213> ORGANISM: Homo sapiens

<400> SEQUENCE: 19

Met Tyr Arg Met Gln Leu Leu Ser Cys Ile Ala Leu Ser Leu Ala Leu
 1               5                  10                  15

Val Thr Asn Ser
            20

<210> SEQ ID NO 20
<211> LENGTH: 29
<212> TYPE: PRT
<213> ORGANISM: Homo sapiens

<400> SEQUENCE: 20

Met Ala Thr Gly Ser Arg Thr Ser Leu Leu Leu Ala Phe Gly Leu Leu
 1               5                  10                  15

Cys Leu Pro Trp Leu Gln Glu Gly Ser Ala Phe Pro Thr
            20                  25

<210> SEQ ID NO 21
<211> LENGTH: 27
<212> TYPE: PRT
<213> ORGANISM: Homo sapiens

<400> SEQUENCE: 21

Met Ala Leu Trp Met Arg Leu Leu Pro Leu Leu Ala Leu Leu Ala Leu
 1               5                  10                  15

-continued

Trp Gly Pro Asp Pro Ala Ala Ala Phe Val Asn
            20                  25

<210> SEQ ID NO 22
<211> LENGTH: 18
<212> TYPE: PRT
<213> ORGANISM: Influenza virus

<400> SEQUENCE: 22

Met Lys Ala Lys Leu Leu Val Leu Leu Tyr Ala Phe Val Ala Gly Asp
1               5                   10                  15

Gln Ile

<210> SEQ ID NO 23
<211> LENGTH: 24
<212> TYPE: PRT
<213> ORGANISM: Homo sapiens

<400> SEQUENCE: 23

Met Gly Leu Thr Ser Gln Leu Leu Pro Pro Leu Phe Phe Leu Leu Ala
1               5                   10                  15

Cys Ala Gly Asn Phe Val His Gly
            20

<210> SEQ ID NO 24
<211> LENGTH: 4
<212> TYPE: PRT
<213> ORGANISM: Artificial Sequence
<220> FEATURE:
<223> OTHER INFORMATION: Description of Artificial Sequence: Synthetic
      linker

<400> SEQUENCE: 24

Gly Gly Gly Ser
  1

<210> SEQ ID NO 25
<211> LENGTH: 4
<212> TYPE: PRT
<213> ORGANISM: Artificial Sequence
<220> FEATURE:
<223> OTHER INFORMATION: Description of Artificial Sequence: Synthetic
      linker

<400> SEQUENCE: 25

Ser Gly Gly Gly
  1

<210> SEQ ID NO 26
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 26
ggtggtggca gc                                                              12

<210> SEQ ID NO 27
<211> LENGTH: 12
<212> TYPE: DNA
<213> ORGANISM: Artificial Sequence
<220> FEATURE:
<223> OTHER INFORMATION: Description of Artificial Sequence: Synthetic
      oligonucleotide

```
<400> SEQUENCE: 27
agcggtggcg gc                                                          12

<210> SEQ ID NO 28
<211> LENGTH: 8
<212> TYPE: PRT
<213> ORGANISM: Artificial Sequence
<220> FEATURE:
<223> OTHER INFORMATION: Description of Artificial Sequence: Synthetic
      linker

<400> SEQUENCE: 28

Gly Ser Gly Gly Gly Ser Gly Gly
 1               5

<210> SEQ ID NO 29
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 29
gccttcagat ctcttctcac ccagaaacgc tggtg                                 35

<210> SEQ ID NO 30
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 30
tcactgatta agcattggtg aagagatctg gttca                                 35

<210> SEQ ID NO 31
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 31
caccagcgtt tctgggtgag aagagatctg aaggc                                 35

<210> SEQ ID NO 32
<211> LENGTH: 35
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 32
tgaaccagat ctcttcactt ggtgatacga gtctg                                 35

<210> SEQ ID NO 33
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 33
```

```
cacccagaaa cgctggtg                                                   18

<210> SEQ ID NO 34
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 34
tcactgatta agcat                                                      15

<210> SEQ ID NO 35
<211> LENGTH: 15
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 35
caccagcgtt tctgg                                                      15

<210> SEQ ID NO 36
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 36
cttggtgata cgagtctg                                                   18

<210> SEQ ID NO 37
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 37
tcactgatta agcataag                                                   18

<210> SEQ ID NO 38
<211> LENGTH: 18
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 38
caccagcgtt tctgggtg                                                   18

<210> SEQ ID NO 39
<211> LENGTH: 7
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 39 ctgatcc                                                                7
```

```
<210> SEQ ID NO 40
<211> LENGTH: 10
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 40
gagacggcga                                                            10

<210> SEQ ID NO 41
<211> LENGTH: 21
<212> TYPE: DNA
<213> ORGANISM: Artificial Sequence
<220> FEATURE:
<223> OTHER INFORMATION: Description of Artificial Sequence: Synthetic
      oligonucleotide  construct

<400> SEQUENCE: 41
ctgatcgcta ggagacggtg c                                               21
```